United States Patent [19]

Newman et al.

[11] Patent Number: 5,050,613
[45] Date of Patent: Sep. 24, 1991

[54] METHOD AND APPARATUS FOR VASCULAR TESTING

[75] Inventors: Dennis Newman, Golden; Gary G. Steffenson, Arvada; Angela G. Willenbring, Westminster; David C. Jones, Arvada; George E. Self, Boulder; Scott N. Wing, Westminster; Alan R. Schmitz, Lafayette, all of Colo.

[73] Assignee: Imex Corporation, Golden, Colo.

[21] Appl. No.: 408,060

[22] Filed: Sep. 15, 1989

[51] Int. Cl.$^5$ ............................................... A61B 5/02
[52] U.S. Cl. .................................. 128/670; 128/691;
128/679; 128/677
[58] Field of Search ............... 128/670, 677, 691, 694,
128/679

[56] References Cited

U.S. PATENT DOCUMENTS

| | | | |
|---|---|---|---|
| 3,570,474 | 3/1971 | Johnson | 128/694 |
| 4,205,688 | 6/1980 | Hausen et al. | 128/694 |
| 4,425,922 | 1/1984 | Conti et al. | 128/691 |
| 4,576,180 | 3/1986 | Taheri | 128/670 |
| 4,718,428 | 1/1988 | Russell | 128/677 |

OTHER PUBLICATIONS

MediaSonics Vascular SA/XT$^{TM}$.
Parks Medical Electronics, Inc., FLO-LAB I, Model 2010.

Primary Examiner—Francis Jaworski
Assistant Examiner—George Manuel

[57] ABSTRACT

An automated vascular testing apparatus includes capillary blood flow sensors and blood pressure detection sensors to detect data regarding the blood flow of a patient. Error detection apparatus insures that the blood data sensors are properly connected and that the output signals therefrom are reliable and provide an adequate basis for measurement. A controller monitors the output signals from the sensors and manages the overall operation of the automated testing procedures. The controller memory temporarily stores the output signals from the blood data sensors, along with other miscellaneous data. A video display presents instructions, data, and conclusions based on accepted medical theories to the operator, while a printer optionally reproduces these data in hard copy form.

43 Claims, 16 Drawing Sheets

| Vascular Diagnostic Report | Date and Time of Report | 08/18/89 10:04:03 |
|---|---|---|
| Patient Number: 524-55-1234<br>Patient Name: J.D. SMITH<br>Birthdate: 02/18/54  Age: 35<br>Height: 069  Weight: 195  Sex: F | Physician Name: DR. F.A. JONES<br>Examiner Name: M.C. DOE | |

Ankle Brachial Index Test

CPT Code: 93910  LOWER EXTREMITY ARTERIES PROCEDURE
ICD-9 Code: ( )440  Athersoclerotic vascular disease
( )443.8  Peripheral vascular disease other specified
( )443.9  Peripheral vascular disease unspecified

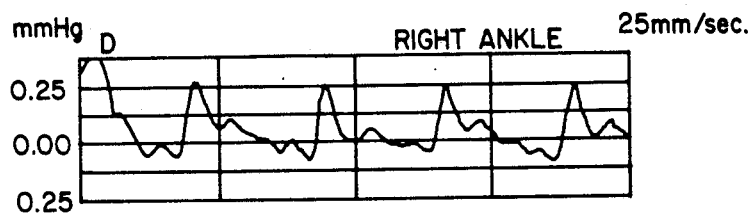

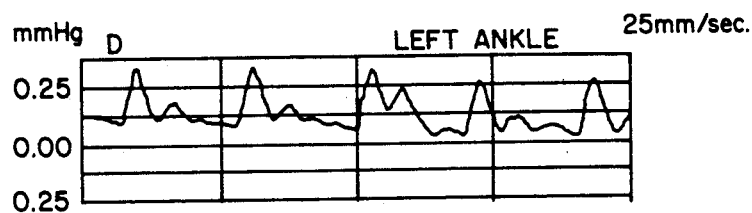

Report of Findings:

| | | | |
|---|---|---|---|
| Right Ankle: | 189 mmHg | Left Ankle: | 192 mmHg |
| Right Brachial: | 180 mmHg | Left Brachial: | 189 mmHg |
| Right ABI = | 1.05 | Left ABI = | 1.02 |

Ankle Brachial Index Chart (*)
Above 0.97
0.71-0.96 - Mild Obstruction
0.31-0.70 - Moderate Obstruction
0.00-0.30 - Severe Obstruction (*) Buchbinder & Flanigan
'Arterial Disease of the
Lower Extremities'

Interpretation

Comments:

FIG. 11

SEGMENTALS TEST

1. Connect RED pressure hose to 10 cm cuff above RIGHT ELBOW.
2. Connect BLUE pressure hose to 10 cm cuff above LEFT ELBOW.
3. Place RED PPG probe on RIGHT INDEX FINGER.
4. Place BLUE PPG probe on LEFT INDEX FINGER.

FIG. 13

METHOD AND APPARATUS FOR VASCULAR TESTING

BACKGROUND OF THE INVENTION

1. Field of the Invention

This invention relates to medical testing systems in general, and to automated vascular testing methods and apparatus in particular.

2. Brief Description of the Prior Art

Vascular testing is a valuable diagnostic tool in determining the overall vascular health of a patient. Over the years, many various tests have been devised and refined to help doctors diagnose conditions and potential problems in the circulatory, or vascular, system of a patient.

For example, a commonly performed vascular test is known in the medical field as an Ankle-Brachial Index or ABI test. Briefly, the ABI test was developed to determine whether an obstruction exists somewhere in the peripheral arteries of the patient. Specifically, the testing procedure measures the systolic pressure in the patient's arm and compares it with the systolic pressure in the patient's ankle while the patient lies in the prone position. The ankle systolic pressure is then divided by the arm, or brachial, systolic pressure to yield the ABI ratio. An ABI ratio greater than 0.97 is usually considered to indicate a normal condition while ratios below 0.97 indicate that an arterial obstruction, such as calculus deposits, might exist somewhere between the patient's heart and the patient's ankle. Such obstructions are usually found in the peripheral arteries since they become continuously smaller in diameter as they continue down the leg.

Until this invention, the ABI test was usually performed manually by a technician who would first have the patient lie in the prone position. The technician would then usually place a conventional sphygmomanometer around the arm of the patient, inflate the pressure cuff while listening via a stethoscope or Doppler ultrasound for the arteries to become occluded. He or she would then slowly deflate the pressure cuff until the arteries re-opened. At that instant, the technician would then record the pressure in the cuff, usually in millimeters of mercury (mmHg), which represents the systolic pressure. Finally, the technician would repeat this procedure on the ankle of the patient. This ankle measurement sometimes posed a problem in that it is often difficult to obtain an accurate determination of when the arteries re-open, and thus the systolic pressure. Once the technician obtained such an ankle systolic pressure, he or she would then manually calculate the ABI ratio based on the two systolic pressures. The technician would also obtain pressure cuff waveforms on each ankle. This testing procedure required a fairly skilled test administrator or technician who could accurately determine when arterial occlusion and arterial re-opening occurred. Since such a determination was usually based to a large degree on the individual judgement of the technician, the test results could vary a certain amount, and were rarely repeatable.

Another common vascular test is known as the Venous Reflux test. The Venous Reflux test was developed to evaluate the competency of the valves in both the superficial and deep venous systems in a patient's legs. The test measures valvular competency by measuring the time it takes for the leg veins to refill with blood after they have been emptied. A rapid refill time indicates a problem with the valves in the leg veins.

The Venous Reflux test is also usually manually performed one leg at a time. In this test, however, the technician usually uses a photoplethysmography (PPG) transducer to optically detect the amount of blood in the capillary system of the leg of the patient, though other detection methods are sometimes used. Briefly, the technician has the patient sit on the edge of a table with the patient's foot resting on the floor. The technician then usually clips or otherwise attaches the photoplethysmography (PPG) transducer, or other such transducer, to the calf of the leg to be tested. This transducer, and its associated detection apparatus, usually had to be carefully calibrated by the technician before the start of the test to assure the accuracy of the detected data. The technician also had to make a judgment call as to whether the patient was sufficiently "rested" before the start of the test, i.e., that the leg veins were filled to capacity and in equilibrium. This was generally done by observing the output signal from the photoplethysmography (PPG) transducer to determine if the signal had reached a steady state value. If, in the judgment of the technician, it had, he or she would proceed with the test. The remainder of the test was administered by instructing the patient to perform a predetermined number of leg flex exercises at some predetermined time interval to pump the blood out of the calf veins. After these flexure exercises, the technician would watch the output signal of the PPG transducer to determine when the steady state signal returned; when it did, the time was recorded. This time is considered to be the venous refill time. Some of the prior art apparatus made a paper strip chart recording of the transducer output signal to be used by the technician as a visual aid in determining the steady state value and the time at which it occurred. However, to a large extent, the accuracy of the test still depended on the skill of the technician in determining first whether the initial steady state had been achieved, i.e., that the leg venous system was completely filled, and second in determining when the second steady state had been achieved indicating that the venous system had completely refilled.

Finally, a Maximum Venous Outflow Test, or MVO test exists to determine whether an obstruction exists in the leg veins. This test uses pneumoplethysmography (PCR), the detection of blood flow by pressure, to measure the blood flow in the leg veins. The maximum venous outflow (MVO), which volume of blood over a given period of time (two seconds is the current standard), is divided by total venous capacitance (VC), which is the total volume of blood that can be held in the leg veins to yield the MVO ratio. An MVO ratio greater than or equal to 0.5 is generally considered to be normal. MVO ratios below this value suggest that veins in the leg may be obstructed.

Procedurally, the MVO ratio has been and can be obtained with generally known procedures as follows. The technician has the patient lie prone with the leg to be tested in a level position but being slightly bent at the knee. A pressure cuff having a pressure cuff recording or PCR transducer, or other such detection means, is wrapped around the calf and slightly pressurized to provide a reliable PCR output signal or waveform. The PCR waveform represents the blood pressure in the calf arteries, and, if the patient is fully "prepared" for the test, represents the equilibrium or baseline value. Typically, this baseline value must be "zeroed" by the technician before the test is initiated, which can be done by adjusting a baseline or zeroing level while simultaneously watching the PCR waveform generated by the pressure cuff transducer. When the technician is satisfied, he or she then places a tourniquet around the upper thigh of the same leg with just enough pressure to occlude the veins but not the arteries of the leg. The technician then observes the PCR waveform, again usually presented on a strip chart, until the wave form has "plateaued," indicating that the veins in the leg have reached capacity. This process can take up to five (5) minutes depending on the patient. Once the leg veins have filled, the technician quickly releases the tourniquet to allow the excess blood trapped in the veins to escape. After the standard 2-second interval, the pressure in the calf is noted, which represents the amount of blood remaining in the calf venous system. The difference between this amount of blood remaining and the amount of blood at equilibrium (the venous capacitance) is the maximum venous outflow or MVO.

The strip chart of the PCR data is manually read by the technician to determine the venous capacitance (VC) and the maximum venous outflow (MVO). After these numbers have been read off the chart the MVO ratio is calculated by dividing the MVO by the VC. Determining the VC is usually straightforward, since it is usually fairly easy to read the value off of the strip chart. However, to determine the MVO, the technician must find the point on the chart that corresponds to the time of tourniquet release and manually scale along the time axis two (2) seconds and calculate the MVO at that point. The physical length of the strip chart can also become quite long if it is allowed to run continuously during the venous fill time. Consequently, many technicians have adopted the practice of manually turning off the strip chart recorder during the venous fill time to save paper and make the chart easier to read. However, the technician must manually turn on the strip chart recorder before untying the tourniquet or t he usable data will never be recorded and the test will have to be repeated.

The foregoing description is intended to provide a generalized background of some of the more common prior vascular tests and the procedures used to implement them. It is not intended to fully describe all of the various tests and testing procedures available in the medical community, but it does provide a general overview of methods used prior to this invention, as well as a preferred embodiment of the present invention. At best, these various vascular test procedures comprise complex procedures, some of which require a significant degree of skill, and which are performed manually or with the aid of various pieces of equipment, such as stethoscopes, tourniquets, Doppler ultrasound detectors, a watch, and the like. Such testing procedures required skilled technicians or physicians who were not only very familiar with the sometimes complex procedures, but also with the anatomical structure and the physical principles involved. These procedures have been time-consuming and require manual handling and operating the components of equipment simultaneously with making judgments relating to zeroing, starting, performing, and stopping while interpreting data. All of this complexity limits available technicians who can handle the procedures competently. Furthermore, since such tests need only be performed on a small percentage of a general physician's patients, most physicians found that it was not cost effective to employ such a skilled technician on a full time basis. Consequently, those patients requiring vascular testing were usually referred to a hospital or a specialized clinic to have the testing performed. Such hospital referrals tended to increase both the costs of the tests and the inconvenience to the patients and usually increased the time period in which diagnoses could be made, since the test results usually had to be sent back to the referring physicians.

SUMMARY OF THE INVENTION

Accordingly, it is an object of this invention to provide improved methods and apparatus for vascular testing.

It is another object of this invention to provide methods and apparatus to perform vascular testing procedures that can be operated competently by persons in the medical services industry under the supervision of a physician, but with a lesser degree of skill, training, and experience than has been required in the past for such tests.

It is a further object of this invention to provide automated methods and apparatus that increase the reliability and accuracy of vascular testing procedures.

It is still yet another object of this invention to provide improved vascular testing methods and apparatus that can reduce the costs and increase the availability and convenience of such tests for both the patient and the physician.

Additional objects, advantages and novel features of the invention will be set forth in part in the description that follows, and in part will become apparent to those skilled in the art upon examination of the following or may be learned by the practice of the invention. The objects and advantages of the invention may be realized and attained by means of the instrumentalities and in combinations particularly pointed out in the appended claims.

In achieving these and other objects, a vascular testing apparatus according to this invention includes a capillary blood flow detection device to detect the instantaneous changes in the capillary blood flow of a patient, and a blood pressure detection device to detect changes in the blood pressure in the veins and arteries of the patient. An error detection device operates in conjunction with the capillary blood flow and blood pressure detection devices to insure that the devices are correctly connected to the vascular testing apparatus and to insure that the output signals therefrom are reliable and will provide an adequate basis for measurement. A controller or computer is connected to the error detection device and to the capillary blood flow and blood pressure detection devices to monitor the output signals therefrom and to control the overall operation of the vascular testing systems. A memory device is also connected to the controller for temporarily storing the output signals from the blood data measuring devices and other miscellaneous data. A display device presents instructions and data to the user or operator, while a reproduction device reproduces such data in tangible form.

The vascular testing methods included with the vascular testing system according to this invention comprise an Ankle-Brachial Index test or ABI test, a Venous Reflux test to determine the competency of the valves in the leg venous system, and a Maximum Venous Outflow (MVO) test to ascertain the sufficiency of the maximum outflow capacity of the leg venous system. Briefly, the ABI test procedure, according to this invention, comprises the steps of first determining the heart rate of the patient and then inflating a brachial pressure cuff and an ankle pressure cuff, which are placed on the patient and connected to the vascular testing system by the operator; continuously displaying the pressure in each pressure cuff on a display device in a real-time format while monitoring the signal outputs from the capillary blood flow detection device to detect arterial occlusion. The method also includes automatically deflating the corresponding pressure cuff at a predetermined rate while monitoring the output signal from the capillary blood flow detection device to detect when the arteries re-open, then determining and displaying the pressure in the pressure cuff at the time of arterial re-opening on the display device as the systolic pressure, calculating the ABI ratio, interpreting it within preset parameters, and displaying it on the display device. The device also obtains pressure cuff waveform at the ankle. All of this information can be printed on a hard copy report.

The method of the Venous Reflux test according to this invention can test both legs individually or simultaneously, and it includes using the output signals from the capillary blood flow detection devices to ascertain whether the venous system is in proper equilibrium for the test to begin. It also includes the steps of continuously displaying the output signal from the blood flow detection device in a real time format throughout the test procedure, and after determining whether the venous system is in equilibrium, visually and aurally cueing the patient to perform flexure exercises in unison with preset timed signals, determining if any datapoints fall outside the display boundaries, and, if so, automatically re-scaling the real-time display. The method of this invention also includes the steps of continuously monitoring and displaying the output signal from the capillary blood flow detection device until the leg veins have refilled with blood, automatically calculating and displaying the refill time, and optionally, printing out of the signal display, the refill time, and a suggested interpretation on a hard copy report. Based on the refill time, the method can also suggest and perform a further tourniquet test.

The Maximum Venous Outflow test process according to this invention includes the steps of monitoring the output signal from the pressure cuff recording detection device, automatically determining a baseline blood capacity level, displaying the output signal in a real-time format, but only for a short time long enough to show the baseline level, automatically inflating a thigh pressure cuff on the patient to a pressure sufficient to occlude the venous system, but not the arterial system, thereby allowing the venous system to fill completely, continuously monitoring the output signal from the blood pressure detection device during this fill time and determining when the veins have completely filled or reached equilibrium, restarting the real-time display of the output signal and continuing this display for a predetermined time, then releasing the pressure in the thigh cuff. The method also includes determining the maximum venous outflow, the venous capacitance, and the maximum venous outflow ratio and displaying those values on the display device. This method can optionally include printing the test data and a suggested interpretation on a hard copy report.

BRIEF DESCRIPTION OF THE DRAWINGS

The accompanying drawings, which are incorporated herein and form a part of the specification illustrate preferred embodiments of the present invention, and together with the description, serve to explain the principles of the invention.

In the drawings:

FIG. 5b is a continuation of the flow chart of FIG. 5a;

FIG. 11 is a representative output display of the results in hard copy report format of the Ankle-Brachial test of the present invention;

FIG. 13 is a representative display of the instructions given at the start of the Segmental Leg test;

FIG. 15b is a continuation of the flow chart of FIG. 15a;

FIG. 19b is a continuation of the flow chart of FIG. 19a;

DETAILED DESCRIPTION OF THE PREFERRED EMBODIMENT

Figure 1:
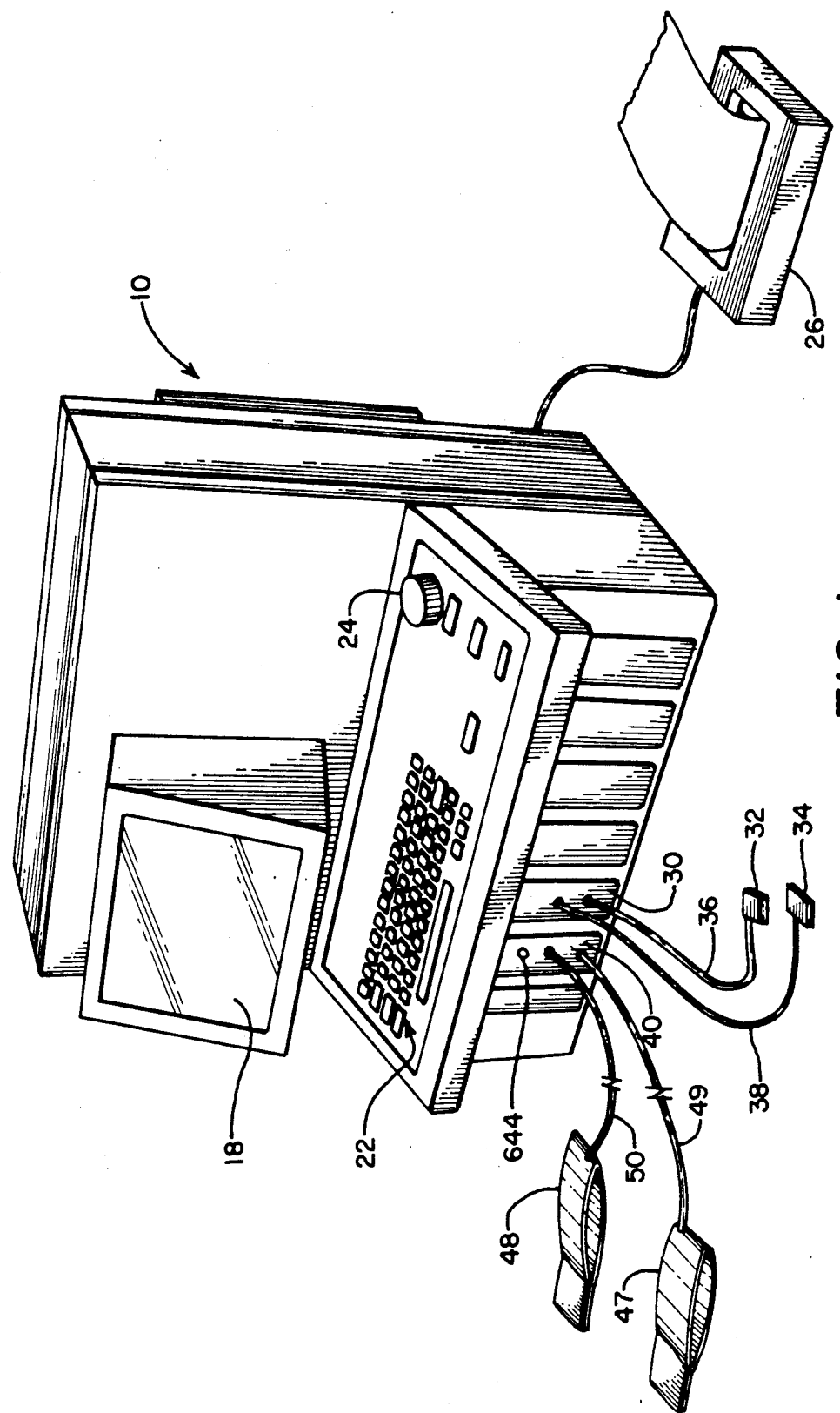
FIG. 1 is a perspective pictorial view of the vascular testing apparatus of the present invention.

The vascular testing apparatus 10 of the present invention shown in FIG. 1 provides a system for the highly automated vascular testing of a patient. In this configuration, the nurse or doctor performing the test interacts with a display screen 18, a keyboard 22, and a dual function selection knob 24. Two pressure cuffs 47, 48 are connected via pneumatic lines 49, 50 to the pneumoplethysmography or PCR module 40. Similarly, two photoplethysmography or PPG transducers 32, 34 are connected via electrical cables 36, 38 to the photoplethysmography or PPG module 30.

In operation, the testing doctor or nurse inputs the appropriate patient data via the keyboard 22 or the dual function selection knob 24 in response to queries displayed on the display screen 18. This patient data is saved in the internal memory 16 and will be printed out by the printer 26 along with the test results at the end of the testing procedure. Once this patient data has been input, the vascular testing apparatus 10 queries the testing nurse or doctor for the particular type of vascular test desired, e.g., an ABI test or a MVO test. Once this test selection is made, the system 10 displays the appropriate instructions for hooking up the pressure cuffs 47, 48 and the PPG transducers 32, 34 to the patient for that particular test. The testing doctor or nurse then wraps the pressure cuffs 47, 48 around the appropriate appendages of the patient, and attaches the PPG transducers 32, 34 to the skin of the patient in accordance with the displayed instructions. The testing doctor or nurse then usually pushes on knob 24 to initialize the testing procedure. As will be discussed in more detail below, most of the testing procedures performed by the system 10 are entirely automated, and require only that the person administering the test move the pressure cuffs 47, 48, or PPG transducers 32, 34, as necessary to the appropriate locations at the appropriate times and to input selections in response to specific queries displayed on the screen 18.

During this automated portion of the testing procedure, the vascular testing apparatus 10 performs a series of hardware calibration tests to ensure that the appropriate transducers are properly calibrated. The system also makes a preliminary examination of the output data signals from the PPG transducers 32, 34 and the pressure transducers 41, 42, checking not only to ensure that the data being received are suitable for measurement, but also to ensure that the patient is properly prepared for the test, i.e., that the vascular system of the patient has reached the proper equilibrium point for the type of test to be performed. Once these initial parameters have been checked and determined to be suitable for testing, the system 10 performs all of the procedures necessary to obtain the test data. For example, during an ABI test, the vascular testing system 10 automatically inflates the pressure cuffs 47, 48 while continuously monitoring the output signals of the PPG transducers to determine when the brachial and ankle arteries are occluded. The system then automatically deflates the pressure cuffs while constantly monitoring the PPG transducer output signals for the moment when the occluded arteries re-open. The pressure in the cuffs at arterial re-opening is noted and displayed on the display screen 18 as the systolic pressure. The system 10 then calculates the ABI ratio, and records the PCR waveform of the ankle for a predetermined time. Finally, the system prompts the testing doctor or nurse that the test has been completed, and instructs the doctor or nurse to repeat the test on the patient's opposite side. After the right and left sides of the patient are tested, the system 10 queries the doctor or nurse for a hard copy printed output. If a hard copy printed output is selected, the system prints out the patient data, test data, ABI ratio, ankle PCR data, and suggested interpretation on the printer 26.

This highly automated vascular testing system 10 of the present invention eliminates the need to manually inflate the pressure cuffs while simultaneously manually determining whether the arteries or veins have been occluded. The system also eliminates much of the guesswork required in the overall testing procedure such as whether the patient is sufficiently prepared, or whether the data being recorded manually are reliable. In sum, since most of the manual steps have been eliminated for a given testing procedure, the overall test results are more predictable and repeatable and therefore allow for a more accurate determination of the overall vascular condition of the patient. Furthermore, since the testing procedure is highly automated, the need for a specially trained technician fully familiar with specific anatomical circulatory structure and the complex parameters involved in the actual test procedures is minimized, thus permitting these tests to be conveniently performed in the doctor's office.

Several other features exist that enhance the operability and convenience of the vascular testing system 10. For example, during each test procedure, the relevant data that are being received from the transducers is displayed in a real-time format on the display screen 18. This real-time display allows the test administrator to visually confirm that the test procedures are being carried out and that accurate and reliable data are being recorded. As was briefly mentioned above, and as will be described more fully below, the system 10 also contains air pumps 45, 46 and solenoid valves 43, 44, represented schematically in FIG. 2, which allow the system to automatically inflate and deflate the pressure cuffs 47, 48 simultaneously or individually, and at precisely controlled times. The pressure transducers 41, 42 not only record pressure data from the cuffs 47, 48, but they also allow the pressure of the cuffs to be precisely controlled. The two independent cuff circuits and PPG transducer circuits also allow for the simultaneous acquisition of data, or allow tests to be simultaneously performed on both the right and left sides of the patient, as will be more fully discussed below.

Figure 2:
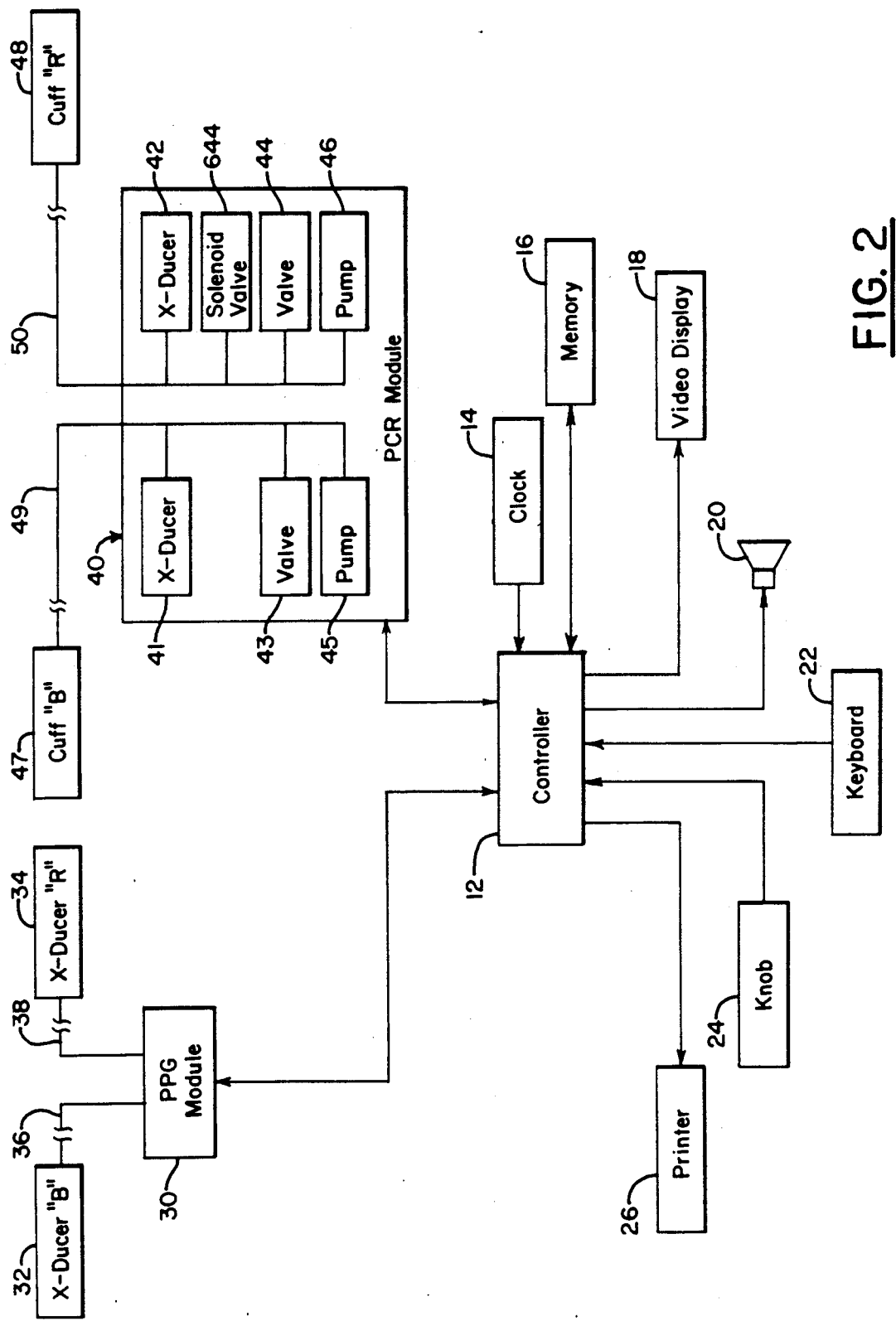
FIG. 2 is a block diagram of the various components of the vascular testing apparatus.

The vascular testing system 10 of the present invention is shown diagrammatically in FIG. 2 and comprises a control unit, or computer 12, a clock 14, a memory device 16, a video display device 18, an audio transducer, or speaker 20, a keyboard 22, a dual function selection knob 24, and a printer 26. A photoplethysmography or PPG module 30 and a pneumoplethysmography or PCR module 40 are used to connect the PPG transducers 32, 34 and the pressure cuffs 47, 48 to the control unit, or computer 12. In operation, the computer 12 receives input signals or data from the clock 14, the memory device 16, keyboard 22, dual function selection knob 24, the PPG module 30, and the PCR module 40, as indicated by the data flow arrows connecting the various components. The control unit or computer 12 also sends output signals or data to the memory device 16, video display 18, audio transducer or speaker 20, and printer 26. The controller also sends output signals to the PPG transducers 32, 34 via the PPG module 30 and to the PCR module to control the operation of the pressure cuffs 47, 48.

Figure 3:
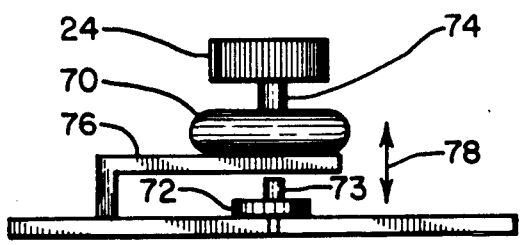
FIG. 3 is a elevation view of the dual function selection knob of the present invention.

The operation and structure of the dual function selection knob 24 is best seen by referring to FIG. 3. Basically, the dual function selection knob comprises an encoder 70 mounted on flexible, resilient mounting bracket 76 above selection switch 72. The encoder 70 detects the rotation of the knob 24 via shaft 74 and converts a finite rotation of the knob 24 into a series of output pulses which are then interpreted by the controller 12 of FIG. 2 to move a selection icon, or highlight, on the display screen 18 among a number of options displayed on the screen 18. Pushing on the knob 24 in the axial direction indicated by arrow 78 causes the bracket 76 to be deflected into contact with an axially moveable actuator 73 to activate the selector switch 72 to select the desired option. Releasing the axial force on the knob 24 allows the resilient bias of the bracket 76 to move bracket 76 upwardly, thereby releasing the actuator 73 and returning selector switch 72 to its normal, or inactive position.

In operation, the dual function selection knob 24 is nearly always used to respond to the queries displayed on the display screen 18. The queries are organized into an appropriate number of options from which the operator is instructed to select. The operator selects the desired response by first rotating knob 24 until the proper test is highlighted, and then by pushing knob 24 to finalize the selection. For example, if the display queries the operator to choose either the ABI test or the MVO test, the operator could select the ABI test by rotating knob 24 until "ABI test" is highlighted and then pushing the knob to make the selection. Extensive use of this query process in combination with the dual function selection knob 24 makes one-handed operation of the device possible while keeping that hand on only the knob 24 without having to move it elsewhere and eases and speeds the operation of the vascular testing apparatus 10 of the present invention.

Figure 4:
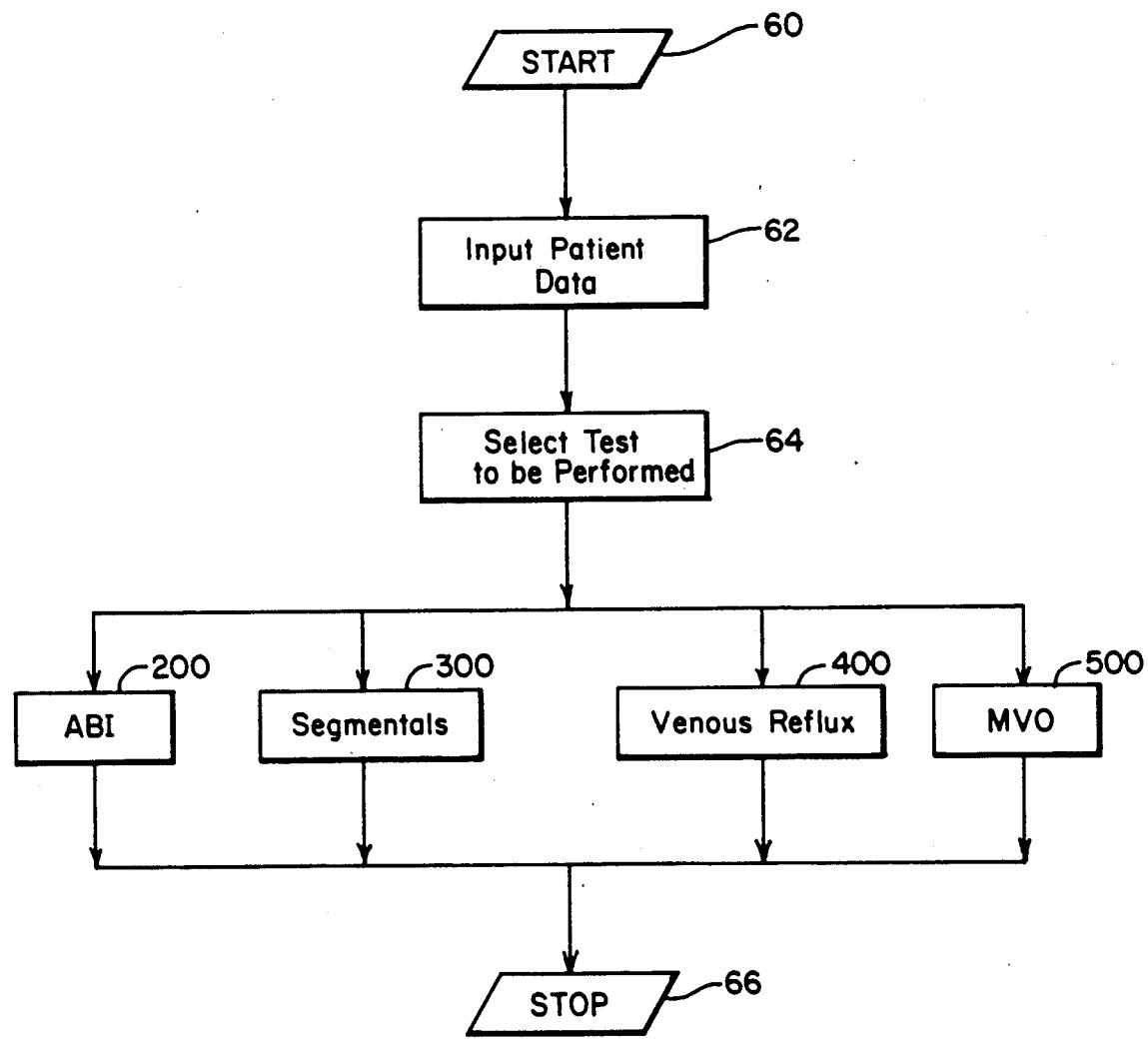
FIG. 4 is a flow chart representation of the overall vascular testing method of the present invention.

The overall method of operation of the vascular testing system 10 is best understood by referring to the flowcharts beginning with the one in FIG. 4. However, before proceeding with a detailed description of the methods described by these flow charts, it is advantageous to briefly discuss how the system 10 of the present invention performs the common vascular tests described above.

The Ankle-Brachial Index, or ABI test can be performed by the system 10, which refers to the test as the "Quicklook ABI Test" for convenience. When the doctor or nurse selects this test, the system displays a series of set-up instructions on the display screen 18. The "Quicklook ABI Test" is initially performed on the right side of the patient, and the instructions correspondingly instruct the test administrator to wrap the pressure cuffs 47, 48 around the patient's right arm and right ankle, and to place the PPG probes 32, 34 on the right index finger and right large toe of the patient. Once these steps are completed, the operator or test administrator presses the appropriate key on the keyboard 18, which causes the system 10 to display an "operating screen." This operating screen 18 displays brief instructions on how to start the test and also presents a real time display of the pressure in each cuff 47, 48. When the test is initiated, the heart rate of the patient is calculated from the output signal from the PPG probe 32 or 34 on the patient's index finger, which optically detects the capillary blood flow of the patient. The operation of such PPG transducers 32, 34 is well known in the art and will not be described in further detail herein. Also, while such optically activated PPG probes 32, 34 are preferred for use with this invention, other transducers that provide similar information or outputs would certainly be suitable. The heart rate is calculated at this stage because it is used in determining when the patient's arteries have re-opened. This procedure will be discussed in great detail below.

As will be more fully discussed below, the system also monitors other attributes of the output signals of the PPG transducers 32, 34 to determine if the signals are accurate enough and reliable enough for the testing process to continue. If no errors in the PPG transducer signals are detected, the controller 12 causes the pumps 45, 46 to inflate the cuffs 47, 48 while a real time display of the cuff pressures is shown on the display screen 18. The cuffs 47, 48 will stop inflating when the system 10 detects, via each PPG probe signal, that the arteries in the arm and ankle of the patient have been occluded. As a safety feature, if occlusion has not been detected by the time the cuffs 47, 48 have been inflated to a pressure of 240 mmHg, the cuffs 47, 48 are immediately deflated and an error message displayed on screen 18. Assuming occlusion is detected, the system 10 causes the cuffs 47, 48 to slowly deflate by actuating bleed valves 43, 44 until the PPG transducers 32, 34 detect that the arteries have once again re-opened. The display screen 18 continues to display the real time cuff pressures. The system 10 establishes a line or mark on the real-time pressure display on screen 18 at the time determined by the controller 12 when the signals from the PPG probes 32, 34, respectively, indicate that the respective arteries have re-opened. This pressure represents the systolic pressure and is also numerically displayed on screen 18 alongside the real time pressure display. The test continues until both systolic pressures have been found.

At this time, both cuffs 47, 48 are deflated to a pressure of about 60 mmHg by the bleed valves 43, 44 and held at that pressure while the system 10 records the output signal from the respective pressure transducers 41, or 42 for the pressure cuff 47 or 48 on the patient's ankle. This output signal is referred to as a PCR signal or a PCR waveform. This signal is recorded and displayed because it is required by most medical insurance plans before the cost of the ABI test will be reimbursed. Once the ankle PCR waveform has been recorded, the system 10 fully deflates both cuffs 47 and 48, calculates the ABI ratio and displays it on the screen 18. The vascular testing system 10 then instructs the operator or test administrator to repeat the test on the patient's left side. When the left side test is completed, the system 10 gives the operator the option by a display on screen 18 of printing a hard copy output of the test results along with an interpretation of those results in accordance with standard medical theory.

If the ABI ratio for the patient is not normal, indicating an arterial restriction or blockage, the operator is given the option to perform another test to more precisely locate the source of the arterial blockage. This test is referred to as the bilateral segmental test or "segmentals test" for short. In this test, the pressure cuffs 47, 48 are sequentially placed at various locations on the patient's legs, usually the ankle, calf, lower thigh, and upper thigh, to determine which segment of the leg contains the obstruction. This test basically tracks the procedures of the Quicklook ABI Test described above, except for the following deviations.

The Segmentals test is performed on the patient's right and left sides simultaneously. Since there are only two pressure cuffs 47, 48 and two PPG probes 32, 34, the procedure cannot determine the ABI ratio for simultaneous brachial and ankle systolic pressures as described above. Instead, the segmentals test determines the systolic pressures in both the left and right arms along with the heart rate. Once the left and right brachial systolic pressures have been determined, the system 10 instructs the operator by display on screen 18 to move both pressure cuffs 47, 48 to the patient's ankles. At this time, the system 10 again automatically inflates and deflates the cuffs 47, 48 to determine the systolic pressure. Next, the system 10 instructs the operator to move both pressure cuffs 47, 48 to the patient's calves, and the lower calf systolic pressures for the left and right sides are determined. This procedure is repeated on the lower and upper thighs of the patient in a similar fashion. After the upper thigh systolic pressures are recorded, the system 10 calculates the ABI ratio for the right and left sides. Like the Quicklook ABI test, the Segmentals test records the PCR waveforms for the ankles, calves, lower and upper thighs and prints them out on the hard copy output along with the left and right ankle-brachial ratio and an interpretation of the results in accordance with standard medical standards.

The Venous Valvular Reflux Test can also be performed by the vascular testing system 10 and is referred to as the "Venous Reflux Test," or Venous Reflux for short. This test is first performed without a tourniquet on the patient, which allows the superficial and deep venous system of the leg to be evaluated. If the results are abnormal, the system 10 instructs the operator to perform the test with a thigh tourniquet to exclude the effect of the superficial system and allow evaluation of the deep venous system only.

Once the operator has selected the Venous Reflux test, the system 10 displays an instruction set on screen 18 which indicates how the patient should be seated and where the PPG probes 32, 34 should be placed. This test is performed on both legs simultaneously. After the PPG probes 32, 34 are placed on the patient, the operator presses the appropriate key on the keyboard 22 to display the operating display on screen 18. This operating display contains real time displays for both the left and right PPG transducer signals. Upon initiation, the system 10 first evaluates the PPG output signals to determine whether the patient is sufficiently "rested", i.e., that the leg venous system is completely filled with blood and is in a state of equilibrium. The specific details of this procedure will be discussed more fully below. If the patient is not fully rested, the system 10 will display an error message on screen 18 and instruct that the patient rest for two more minutes. If the patient is fully rested, the test proceeds by cuing the patient, both visually on the display 18 and aurally via the speaker 20, to flex his or her legs in timed unison with each cue signal. The number and duration of these flexures is standardized in the medical community for performing this type of test. The effect of the flexures is to pump the blood trapped in the leg veins to the upper body where it is returned to the heart.

The system 10 notes the time of the last flexure exercise by automatically placing a "caliper" on the real time display on screen 18. At this time, the system 10 also re-scales the display if any of the datapoints from the PPG signals fall outside of the default scale setting. This re-scaling procedure is a significant feature of this invention that can save time by eliminating the common need to put the patient through the above-described preparatory procedure several times while trying to find an appropriate scale, as has been the practice in the past. It will also be more fully described below.

The system 10 then monitors the PPG signals until it detects a "plateau", indicating that the leg veins have refilled. When this plateau is detected, the system 10 automatically places a second caliper at that point on the real-time signal display on screen 18 and determines the refill time by automatically measuring the elapsed time between the two calipers. This refill time is then displayed along with an interpretation of whether the time is normal or abnormal. If the refill time is abnormal, the system 10 will recommend that the tourniquet test be performed. Finally, the system 10 also gives the skilled operator the option to move the location of the second caliper, thereby changing the time and the results, via the dual function control knob 24, if the operator thinks, based on his or her independent judgment, that the plateau occurred elsewhere. Usually, however, the ordinary operator will use the caliper setting made by the system 10.

The tourniquet test is very similar to the above-described test, except that the system 10 instructs the operator to place a pressure cuff on the right or left leg of the patient, i.e., whatever leg was abnormal. If both legs tested abnormal, the system 10 instructs that pressure cuffs 47, 48 be placed on both legs of the patient. In this test, the pressure cuffs 47, 48 are used by the system 10 in a manner such that they function as a precisely regulated tourniquet. When the test is initiated, the system inflates one or both of the pressure cuffs 47, 48 to a pressure of approximately 60 mmHg, which is just enough pressure to occlude the superficial veins, but not the deep veins or leg arteries. This pressure will be maintained and is displayed on the operating display on screen 18, while the above flexure test is repeated. As before, the second or plateau caliper can be optionally adjusted by the operator if necessary. The results and interpretation can also be printed on the printer 26.

Lastly, the Maximum Venous Outflow Test, or MVO test can be performed by the vascular testing system 10 of the present invention. Briefly, this test uses the output from the pressure cuff transducers 47, 48, referred to herein as the PCR output or PCR waveform, to asses the blood flow in the legs. The system 10 uses the PCR data to determine both the venous capacitance (VC) and the maximum venous outflow (MVO) which is the amount of blood that flows through the leg veins in the standardized time period (currently 2 seconds). The venous capacitance (VC) is divided by the maximum venous outflow (MVO) to yield the MVO ratio.

Selection of this test first generates an instruction display that directs the operator to wrap one pressure cuff, such as 47, around the patient's ankle and the other pressure cuff, such as 48, around the patient's upper thigh. A unique feature of the present invention is that it automatically prepares the patient's leg venous system by the following procedure. The thigh cuff 48 is first automatically inflated to a pressure of approximately 55 mmHg which is enough to occlude the entire leg venous system, but leaves the leg arteries open. This allows blood to continue to flow into the leg, but it cannot escape. This results in a slight stretching of the leg veins below the thigh tourniquet as they fill with blood. The thigh pressure is held for about two minutes and is then released, which allows the pooled blood to escape. This procedure is performed a total of three times to properly prepare the leg for the test. The reason for the preparation procedure is that it results in the more accurate determination of the venous capacitance.

After the leg has been prepared, the system 10 automatically proceeds to the actual test. The calf pressure cuff 47 is inflated automatically to about 15 mmHg and the system 10 checks for pressure errors or leaks. The thigh cuff 18 is then inflated automatically to a pressure of about 55 mmHg and allowed to stabilize. At this point the system 10 displays approximately 2 seconds of PCR data from the calf cuff 47 on the display screen 18 to show the baseline pressure level. The display is then automatically paused until the venous system completely refills and the plateau in the signal is detected by the system 10. The real time display is then started again to show the calf PCR trace for the remainder of the test. Approximately four seconds after the display is restarted, the system 10 quickly deflates or dumps the pressure in the thigh cuff 48, thus allowing the blood trapped in the leg to escape. A first caliper is automatically placed by the system 10 on the display on screen 18 at the precise instant of pressure release or dumping. Two seconds later, another caliper is automatically placed by the system 10 on the real-time display on screen 18, and the remaining pressure in the calf cuff 47 is dumped. The system 10 automatically determines maximum venous outflow by looking at the trace data at the time of the thigh cuff dump and two seconds later, i.e., where the system 10 placed the two calipers respectively. The difference in the signal amplitude at these two calipers (the maximum venous outflow) is compared to amplitude of the plateau (the venous capacitance) to yield the MVO ratio. The venous capacitance, the maximum venous outflow and the MVO ratio are then displayed along with the PCR trace.

A convenient feature of this test procedure is that the real time display is automatically stopped during the venous fill time, since this data is of no use anyway. This allows the entire PCR trace to be displayed in a compact format, thereby eliminating the need for the operator to manually turn off the strip chart recorder during the refill time and manually turn it back on at the plateau to avoid producing an excessively long strip chart recording.

This above general description of the various testing procedures that can be performed by the system 10 of this invention should facilitate the following detailed description of the preferred embodiment of the invention.

The method of the present invention is most easily performed by programming the computer 12 to execute the steps of the method of the invention. Therefore, the following description will refer to conventional flow charts to explain the detailed processes of the method.

The overall method of operation of the vascular testing system of the present invention is best understood by referring to FIG. 4. After the initial start procedure 60, the system 10 prompts the operator to input the patient data at step 62. This data is stored in the memory device 16 for later use in printing the permanent outputs. The system next queries the operator to select the desired test at step 64. For the purposes of this invention, only four (4) alternatives 200, 300, 400, and 500 are shown in FIG. 4. These alternatives correspond to the four common vascular tests described above and comprise the quicklook ABI test 200, the Segmentals test 300, the Venous Reflux test 400, and the Maximum Venous Outflow test 400. Other tests are performed by the vascular testing system 10, but they are outside the scope of this invention. Detailed descriptions of the steps 62 and 64 are not given, since it is well known in the art to program a computer to generate user interactive queries that allow an operator to select one of a number of predetermined choices.

Figure 5A:
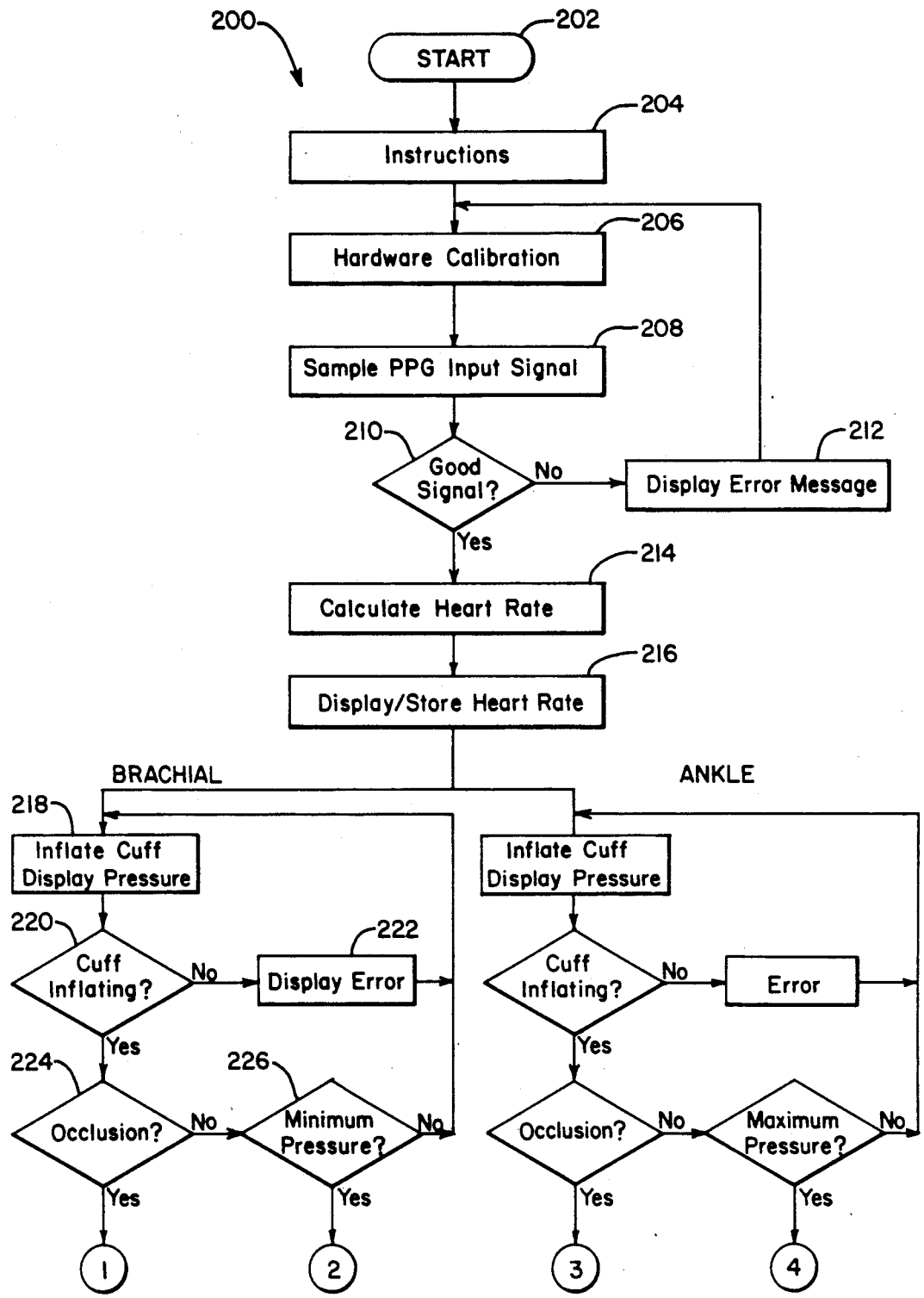
FIG. 5a is a detailed flow chart of the Ankle-Brachial Index test of the present invention.

The method of the quicklook ABI test 200 is best understood by referring to FIGS. 2, 4, 5a, 5b, 6, 7 and 8. Referring to FIG. 5a, the quicklook ABI test 200 is initiated by the start sequence 202 in which the operator selects this test from a menu of tests shown on display screen 18 at step 64 in FIG. 4. After the start sequence 202, the computer 12 proceeds to step 204 that displays several instruction pages, the first of which is shown for illustration purposes in FIG. 6. This display instructs the operator to insert the "red" pressure hose 49 into the pressure cuff 47, and wrap that pressure cuff on the patient's arm above the patient's right elbow. These instructions also instruct the operator to insert the "blue" pressure hose 50 into the pressure cuff 48, and wrap that cuff around the patient's right ankle. Likewise, the instruction display shown in FIG. 6 directs the operator to place the red PPG probe 32 on the patient's right index finger and the blue PPG probe 34 on the patient's large right toe.

The color designations "red" and "blue" are used to designate the "channel" of a particular cuff, or the channel of a particular PPG probe. In the preferred embodiment, the red coded transducers are usually for the patient's right side, and the blue coded transducers are usually for the patient's left side. However, this is not the case for the Quicklook ABI test since the test is only performed on one side of the patient at a given time. In this case, the color codings help prevent the operator from intermixing the cuffs and PPG probes. Note that any suitable identification scheme could be used in place of the above, and the present invention should not be considered as limited to any particular designation scheme.

Referring back to FIG. 5a, the method next proceeds to step 206 to initialize any particular hardware requiring initialization, and calibrate the PPG probes 32 and 34. The specific hardware that might need to be calibrated would vary depending upon the particular hardware implementation used and the particular hardware calibration requirements would be obvious to someone skilled in the art of making vascular diagnostic equipment.

The PPG probe calibration procedure used in the preferred embodiment is somewhat complicated, but is performed as follows. First, the PPG output signals are analog in nature and are amplified and converted into a digital signal that can be used by the controller 12 by analog to digital converters (A/D converters). These A/D converters divide the analog signal into a digital signal which ranges in value from +4096 bits or counts, to −4096 bits or counts. Since the analog PPG signal must be amplified before it can be converted, the signal level may not always be exactly zero when shorted to ground. For example, after the signal is converted into digital format, the zero line may float between, say +16 bits and −4 bits. The calibration process accordingly notes the bit level of this floating zero line when the probe outputs are shorted to ground, and correspondingly adds or subtracts an offset bit amount to all subsequent digital signal levels to provide a true zero level. Specifically, the PPG probes 32, 34 are calibrated by shorting both of the signals to ground, waiting approximately 7 seconds, and then reading both signal levels in the digital format. These values are stored and used as line offsets as will be more fully discussed below. The PPG probes 32, 34 are then unshorted and allowed to stabilize for about 7 seconds. Different procedures might need to be used for different types of PPG transducers, and the methods of calibrating them are well known and will not be further discussed herein.

Figure 8:
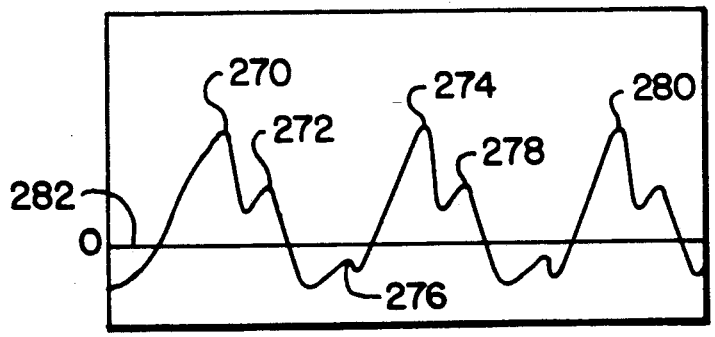
FIG. 8 is a sample of the PPG transducer output signal showing the various peaks in typical heartbeat.

After step 206, the system 10 proceeds to step 208 to evaluate whether the PPG probes are generating a reliable signal. Since the PPG transducer signals are used to determine whether the arteries have been occluded, it is essential that their respective outputs have sufficient signal strength and low noise to enable the reliable detection of blood flow. A sample PPG waveform is shown in FIG. 8. Basically, step 208 evaluates the output signal of each PPG transducer 32, 34 for a period of about 4 seconds. Three peaks, such as 270, 272, and 274 with amplitudes greater than 25 bits or counts in the digital format should be detectable within this time period. If three such peaks are not detected, decision process 210 prints an error message 212 that instructs the operator to reposition the corresponding probe in hopes of obtaining a stronger signal. This process is repeated until a good PPG signal output is attained.

Step 214 calculates the heart rate of the patient based on the waveform generated by the PPG transducer 32 placed on the patient's index finger. Many methods exist for determining the heart rate of a patient based on a PPG output signal as shown in FIG. 8. The following description describes the method used in the preferred embodiment, though other methods exist and can be substituted therefore. The present invention hence should not be construed to be limited to the particular heart rate detection method described herein.

Basically, the heart rate detection algorithm used in the present invention uses a slope detection method to find the positive peaks 270, 272, 274, 276, and 278 of a typical PPG signal such as that shown in FIG. 8. Essentially, the data signal are evaluated on a point by point basis to find the location of the transition points between positive and negative slopes. The method requires that two adjacent data points be of the same polarity or slope value below the zero line 282 before a slope change decision is made. Thus, in FIG. 8, points 270, 272, 274, 278, and 280 would be such transition points or peaks. Cusps, such as point 276 are not considered peaks because point 276 lies below zero line 282.

Mention should be made here of the earlier process 206 that calibrated the PPG probe signals by recording an offset value. This offset value is subtracted from all incoming data such that the output signal has a meaningful zero line 282. This step is essential in determining the correct valve for the maximum peak amplitude for the PPG signal which is stored in memory 16 for later use.

An initial heart rate is now calculated based on the amount of time between peaks 270, 272, 274, 278, and 280. This calculation is based on the average of the times between any four peaks such as 270, 272, 274, and 278 according to the following equation:

$$\text{heart rate} = \frac{60}{(t_{272} - t_{270}) + (t_{274} - t_{272}) + (t_{278} - t_{274})}$$

If this number is greater than 100 beats per minute (bpm) or less than 30 bpm the data is re-analyzed. The reason these data need to be re-analyzed is that noise signals, or excessively strong dichrotic notches (i.e. the "notch" between peaks 270 and 272) have created a false number of signal peaks.

Figure 9:
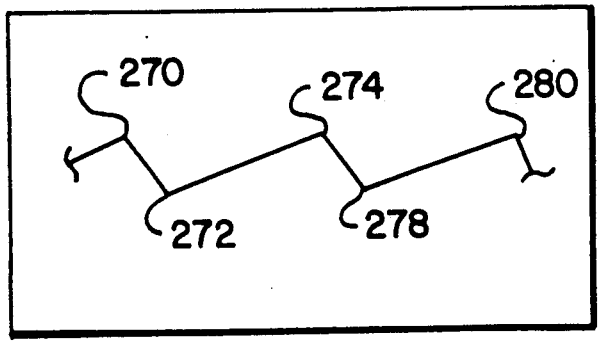
FIG. 9 is a simplified display of the output signal of FIG. 8 showing the relative positions of the signal peaks.

The re-analyzation method is best understood by referring to FIG. 9. Points 270, 272, 274, 278, and 280 are shown in relative relation to one another as they appeared in FIG. 8. By using a slope detection method, those peaks that are preceded by negatively sloped line and followed by a positively sloped line are eliminated. Thus peaks 272 and 278, which represent dichrotic notches, are thrown out and the heart rate equation is recalculated using the four "real" peaks 270, 274, 280 and the next peak, not shown in FIGS. 8 or 9. If the heart rate falls between 30 and 100 bpm the process is complete. This heart rate detection method provides a reliable heart rate calculation for the variety of waveforms present from very diseased to normal patients.

Figure 10:
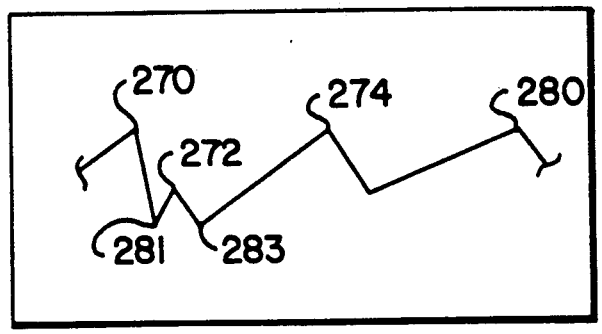
FIG. 10 is a simplified display of a "noisy" or "ragged" PPG signal similar to that of FIG. 9, but showing two additional peaks.

Occasionally, however the incoming PPG data signals contain fairly large ragged peaks which will result in an inaccurate heart rate even after the data has been re-analyzed as described above. In this case, a relative peak size detection method is used to further filter the signal. This method is best understood by referring to FIG. 10. Suppose the simplified signal of FIG. 9 contains two additional peaks 281, 283 disposed between peak 272 that are a result of a ragged input signal. The slope detection process would then have eliminated points 281 and 283, but would have left point 272. This extra point is then responsible for the still too high heart rate. If this happens the relative peak size detection method is invoked which eliminates all peaks outside +/− 45% maximum peak amplitude range that was determined earlier. The effect is to eliminate peak 272 which results in an accurate calculation of the heart rate.

Figure 7:
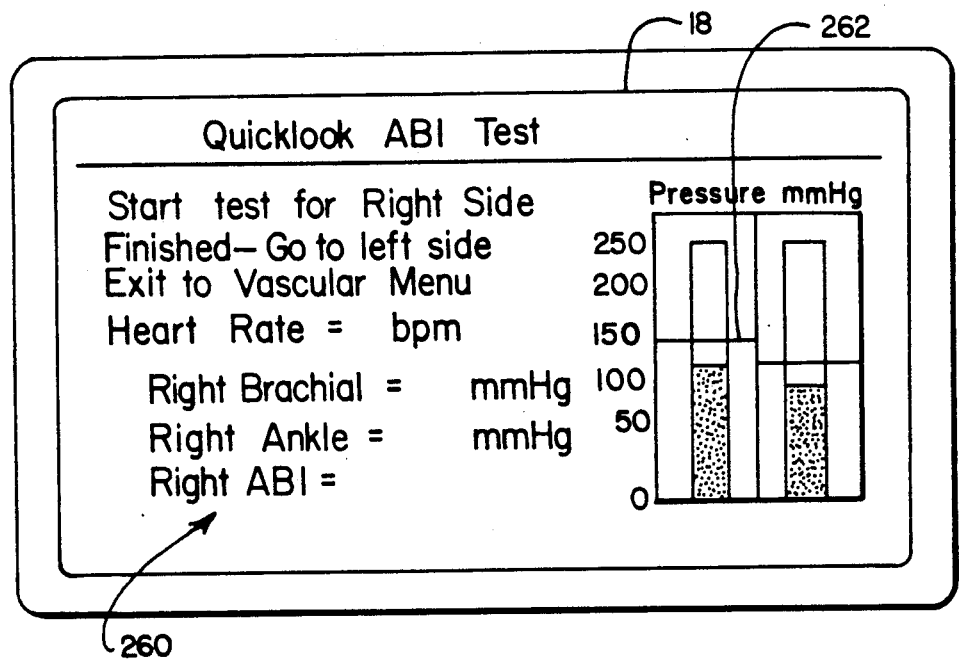
FIG. 7 is a representative display of the operating screen of the Ankle-Brachial Index test showing the real time pressure display.

After the heart rate is calculated, the maximum peak amplitude value previously stored in memory 16 is used to calculate an occlusion cut-off value. The occlusion cut-off value is 75% of the maximum peak amplitude for each PPG signal, or 200 bits or counts in the digital format, whichever is smaller. Finally, the heart rate is displayed by step 216 and shown on the display screen as illustrated in FIG. 7.

Figure 5B:
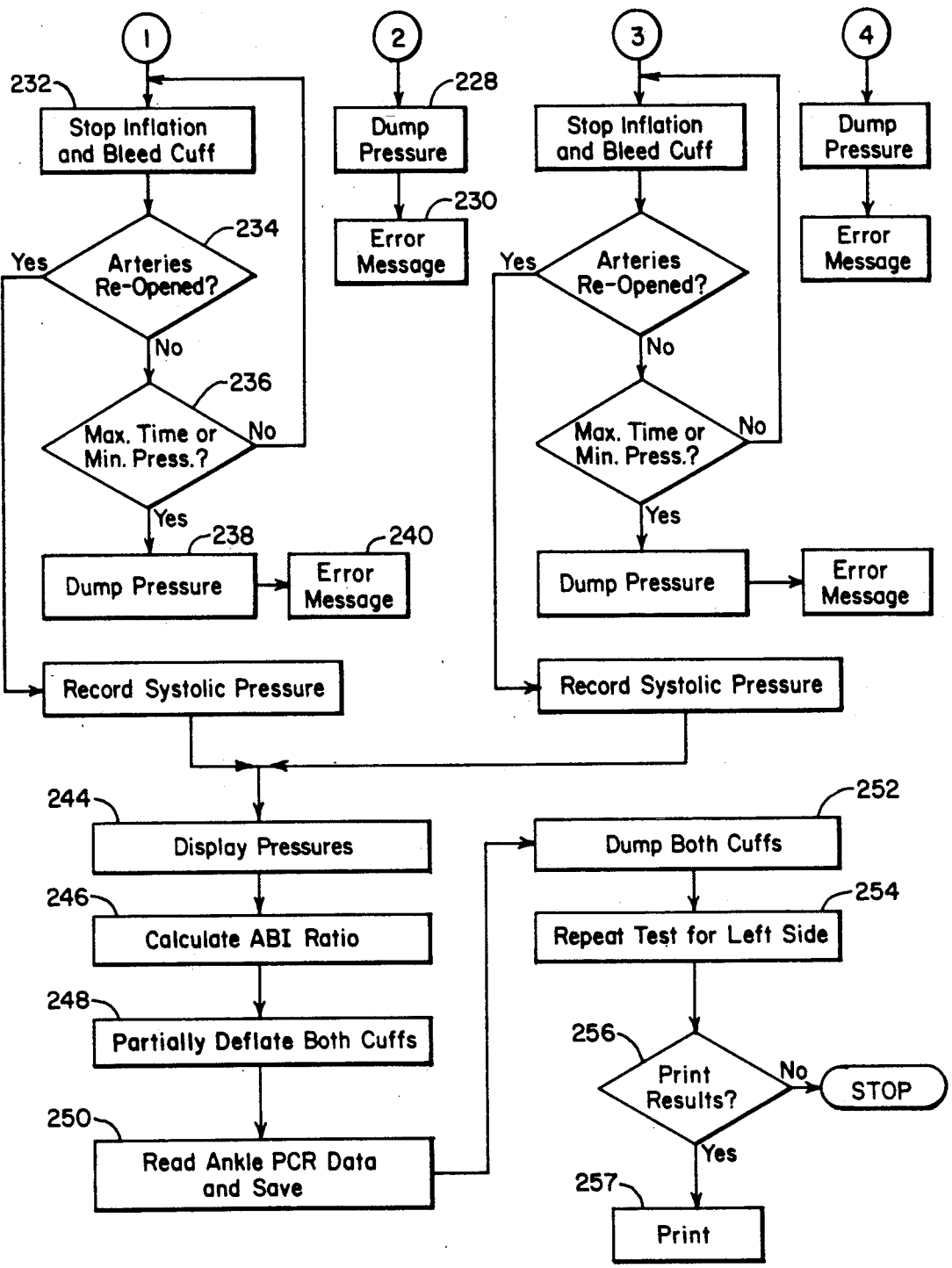
Figure 6:
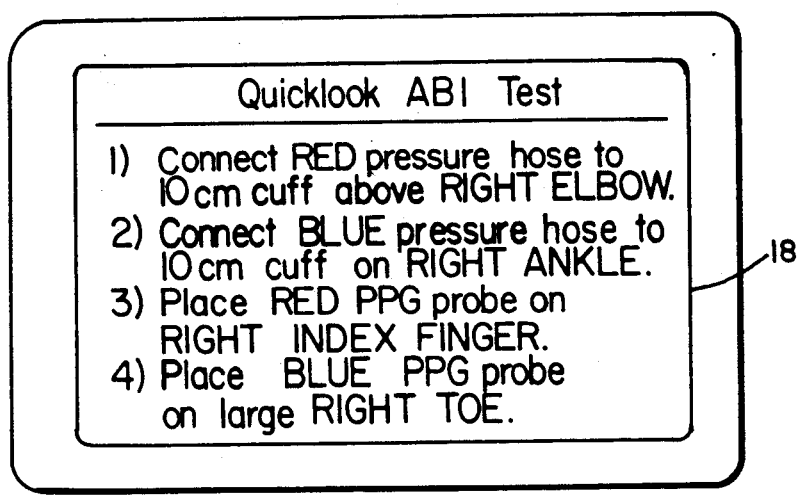
FIG. 6 is a representative display of the instructions given at the start of the Ankle-Brachial Index test.

Having accurately determined the patient's heart rate according to the above procedure, the system 10 next proceeds to simultaneously inflate the brachial and ankle pressure cuffs 47 and 48. Referring to FIGS. 5a and 5b, only those steps for the brachial cuff 218-242 are numbered and described in detail. The steps for the ankle cuff 48 are identical to those for the brachial cuff 47 and will not be described in detail for the sake of brevity.

The process 218 activates pump 45 which begins inflating the brachial cuff 47. The pressure of the cuff is detected by transducer 41 and is continuously displayed in a real time manner on the display shown in FIG. 7. Decision process 220 checks to see if the cuff is inflating properly. Specifically, if a pressure build-up is not detected within 3 seconds of pump actuation, the system displays an error message 232 asking the operator to recheck the hose connections. If the pressure cuff is inflating properly, the method proceeds to process 224 to determine whether the arteries in the patient's arm have been occluded. If the arteries are not occluded, the flow continues to step 226 which checks to see if a maximum pressure or time has been reached. Specifically, if the pressure has reached 240 mmHg or if the time has exceeded 2 minutes, the program dumps the pressure in the cuff at step 228 and displays an error message 230. This safety check 226 is performed because the arteries of some patients, for example diabetics, cannot be occluded except at dangerously high pressures.

The occlusion detection process 224 analyses the amplitude of the PPG signal peaks. Once the peak amplitude is less than or equal to the occlusion cut-off value previously calculated, arterial occlusion has occurred, and the pump 45 is deactuated and the bleed valve 43 is opened at step 232. This process continues until step 234 detects that the arteries have reopened. If two minutes elapses and arterial re-opening has not yet occurred, or if the pressure in the cuff has dropped below 40 mmHg, step 236 dumps the remaining pressure in the cuff at step 238 and an error message is displayed at 240.

The step of arterial re-opening detection 234 monitors the PPG signal until a systolic peak is detected. A modified slope detection method is used to detect peaks in the PPG output signal. In the preferred embodiment, the peaks in the PPG output signal will be treated as systolic peaks if they have a positive slope with a time duration of greater than or equal 48 milliseconds and less than 180 milliseconds. These detection criteria eliminate a large percentage of the random and background noise present in the PPG output signal. Additionally, to qualify as a systolic peak, a peak must be followed by three other peaks, each of which must fall within +/− 25% of the calculated heart rate time.

The particular blood pressure detection method, occlusion determination method, and arterial re-opening detection method described above have been continually refined through experimental testing and represent the best mode of obtaining those data. Other methods, however, currently exist and still other methods of accomplishing the same goals could be developed in the future. These methods have been described in detail in the interest in providing an enabling embodiment for the invention and the use of other methods of determining heart rate, and the time of arterial occlusion and re-opening should be considered within the scope of the present invention.

Referring again to FIG. 5b, once the brachial arteries have re-opened as detected by step 234, the process proceeds to step 242 that records the pressure in the cuff at the instant the artery has re-opened. As discussed earlier, this pressure represents the systolic pressure in the brachial arteries which is then displayed at step 244 on the display screen 18 both as a number 260 and as a line 262 across the real-time pressure display as shown in FIG. 7.

When both the brachial and ankle systolic pressures have been obtained and displayed, the system 10 calculates the ABI ratio at step 246. Both pressure cuffs 47, 48 are then automatically deflated to about 60 mmHg pressure in step 248. Next, step 250 reads and saves the PCR waveform from the ankle pressure cuff for a predetermined period of time. In the preferred embodiment, four seconds of ankle PCR data are read and stored by the system 10. These ankle PCR data, which is really the arterial ankle pressure waveform, as seen in FIG. 11, are of no relevance in the determination of the ABI ratio, but most insurance companies require such data to accompany the results of the ABI test.

Once the ankle PCR data is saved for later printout, the system 10 dumps the remaining pressure in both pressure cuffs 47, 48 at step 252 and instructs the operator to repeat the test for the left side of the patient at 254.

After completing the Quicklook ABI test for the left side, the system 10 asks the operator if he or she wants a hard copy printout at step 256. If a hard copy printout is requested, the system prints the test results at 257. Such a sample output is shown in FIG. 11.

Figure 12:
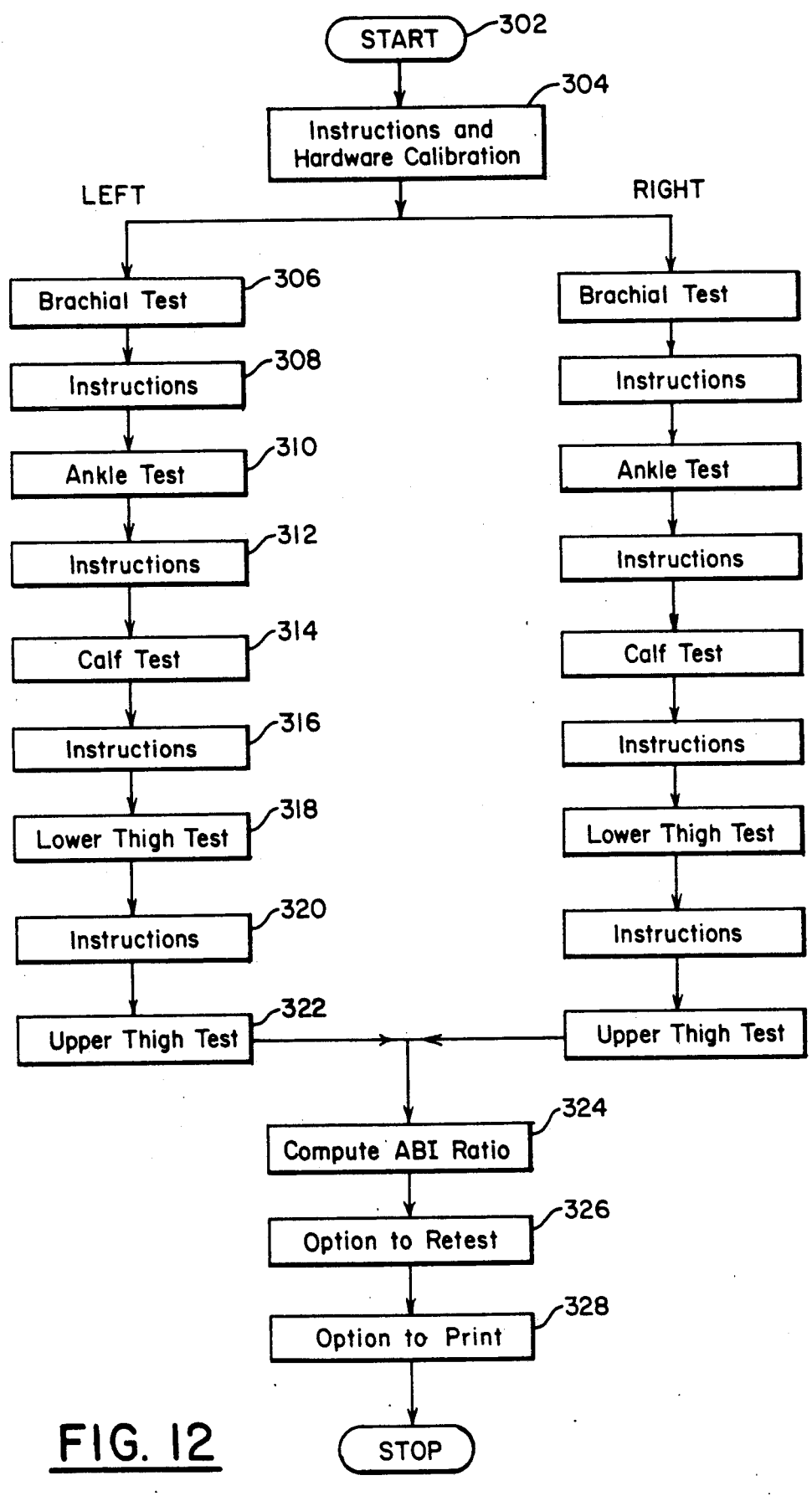
FIG. 12 is a detailed flow chart of the Segmental Leg test of the present invention.

The method of the segmental leg test, or segmentals test 300 is best understood by referring to FIG. 12. This test functions in much the same way as the Quicklook ABI test 200 except that the systolic pressures are calculated in a different order. FIG. 12 accordingly only shows the general flow of the segmentals method 300 and does not repeat the specific steps of determining the systolic pressures, calculating the ABI ratio and recording and saving the various PCR waveforms.

Once the start sequence 302 is selected, the process proceeds to step 304 where the specific instructions for administering the test are displayed on the screen 18 as shown in FIG. 13. The main difference between the segmentals test 300 and the Quicklook ABI test 200 is that in the segmentals test, the systolic pressures are obtained for the left and right sides of the patient simultaneously. Thus, the steps shown in FIG. 12 for the patient's right side are identical to the steps for the left side. Consequently, the right side steps, while shown in FIG. 12, are not numbered and will not be discussed in detail.

After the initial instruction and hardware calibration is completed in step 304, the method executes step 306 which, like the ABI test 200, measures the patient's heart rate, inflates the left brachial cuff 48, looks for arterial occlusion, deflates the cuff until the arteries re-open, and measures and displays the systolic pressure. This same process is performed simultaneously on the patient's right arm as shown in FIG. 12.

Figure 14:
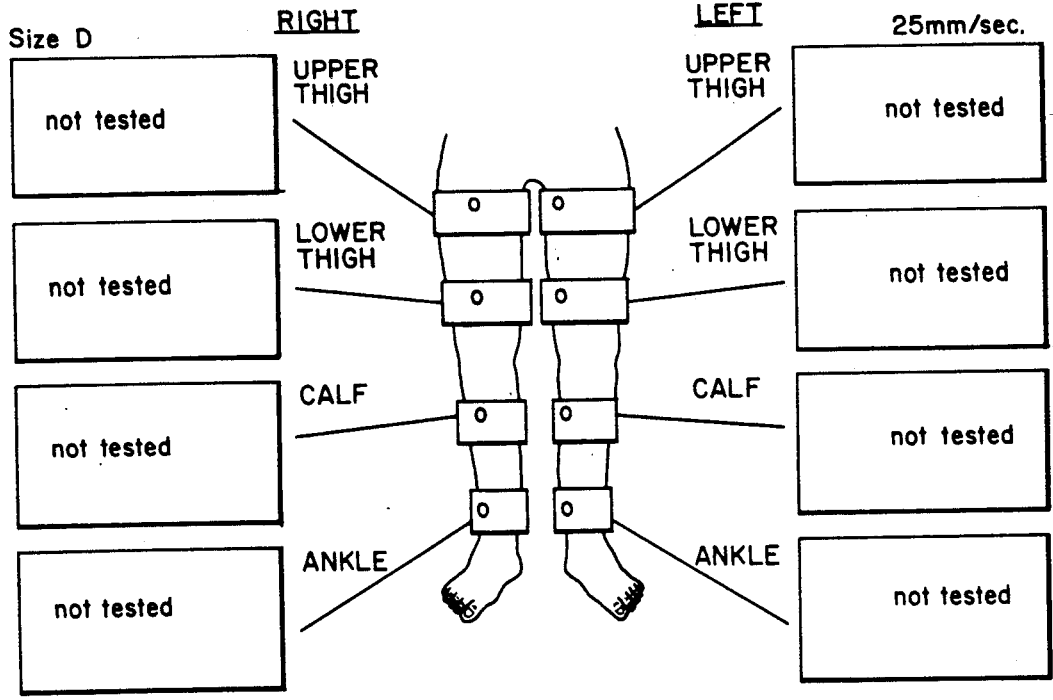
FIG. 14 is a representative output display of the results in hard copy report format of the Segmental Leg test of the present invention.

After both the left and right brachial systolic pressures have been recorded, new instructions are displayed at step 308 which direct the operator to move the pressure cuffs 47, 48 to the patient's left and right ankles where the entire test is repeated at step 310. The heart rate is not measured at this stage since it was already determined in step 306. However, after the systolic pressures are obtained, the process records and saves the PCR waveform for the ankles. Again, this PCR waveform is usually required for insurance reasons only. This same procedure is repeated for the patient's calves, lower thighs, and upper thighs as shown by steps 312 through 322. After the upper thigh systolic pressures and PCR waveforms have been recorded, the method computes the left and right ABI ratios at 324. Step 326 gives the operator the option to repeat the test at any of the above locations. If any of the locations are retested, the old data is discarded and replaced by the new test data, and the ABI ratio is recalculated if necessary. As always, the operator can request a hard copy output which is printed out at step 328. A sample of such an output is shown in FIG. 14.

Figure 15A:
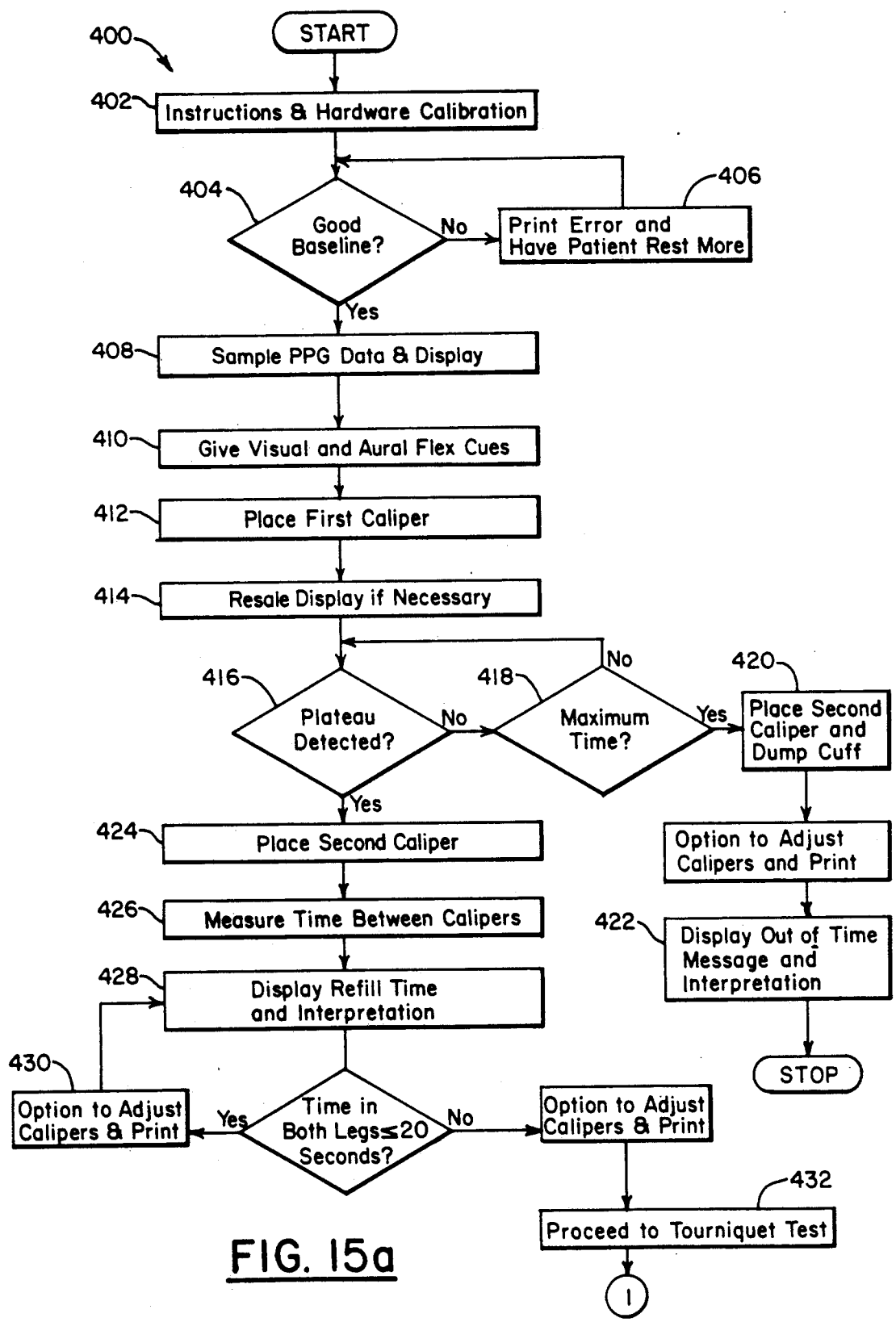
FIG. 15a is a detailed flow chart of the Venous Reflux test of the present invention.
Figure 15B:
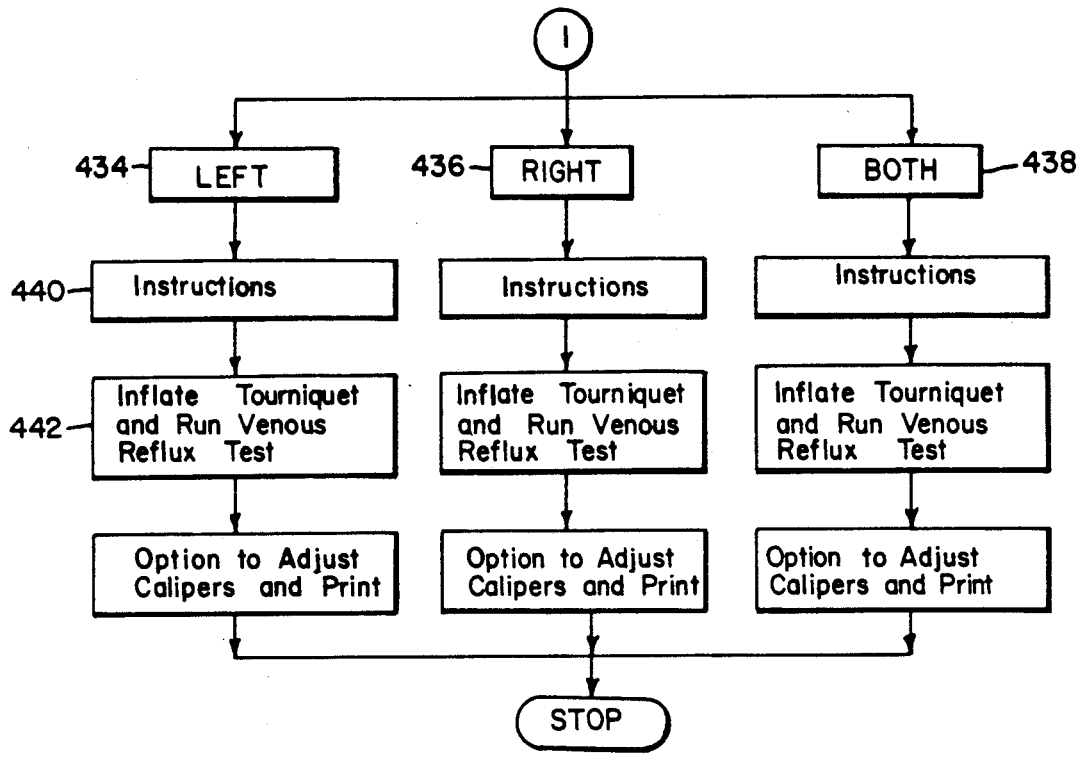
Figure 16:
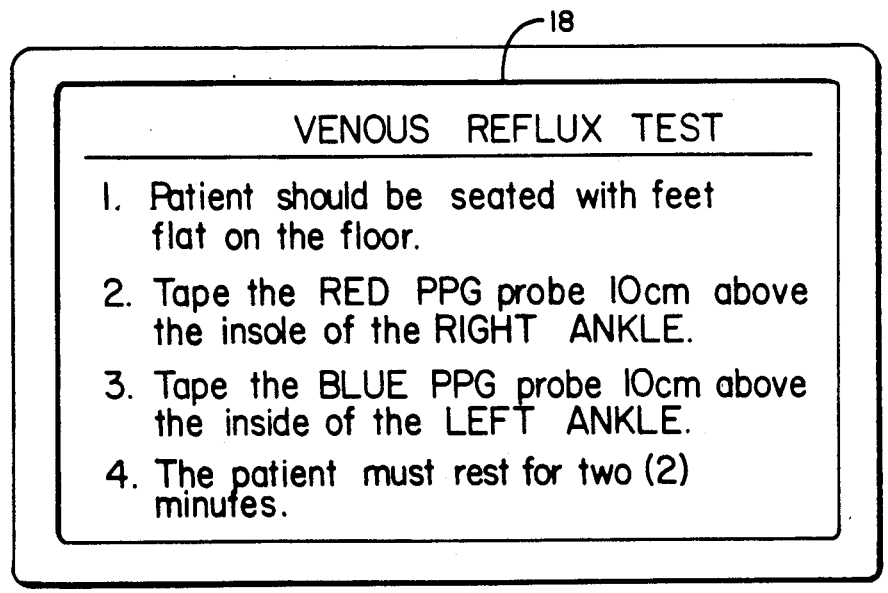
FIG. 16 is a representative display of the instructions given at the start of the Venous Reflux test of the present invention.
Figure 17:
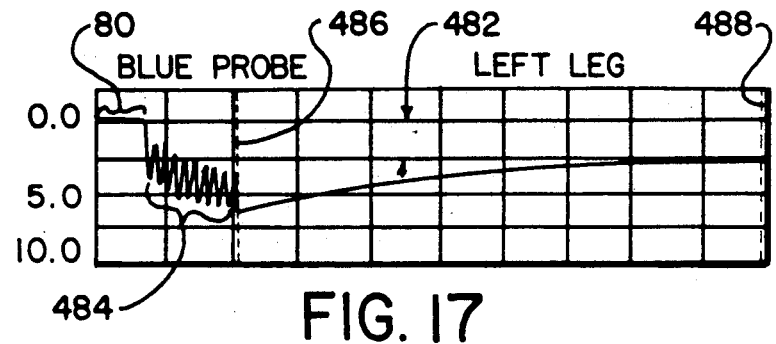
FIG. 17 is a representative sample of the output signal from a PPG transducer for the Venous Reflux test of the present invention.

The operation and method of the venous reflux test 400 is best understood by referring to FIGS. 15a and 15b. Initiation of the Venous Reflux test starts the instruction display and hardware calibration process 402. A sample of the introductory display is shown in FIG. 16. As with the ABI test 200, the hardware calibration step calibrates any specific hardware so requiring calibration and further calibrates the PPG probe output signals by establishing the line offset values for each probe signal as described above. After calibration, each PPG output signal is sampled for a predetermined time (5 seconds in the preferred embodiment) to make sure that a steady state, or baseline value exists. This baseline value is indicated by region 480 in FIG. 17. If this value varies by more then a certain amount in this predetermined sample time, it is an indication that the patient's venous system has not reached equilibrium which would result in inaccurate test data. If this is the case, an error message is displayed, and the patient is asked to rest for approximately 2 more minutes at step 406.

In the preferred embodiment, if the baseline trace 480 varies by more than +/− 0.44 of a grid 482 during the 5 second period, the patient has not sufficiently stabilized. These specific values and time periods have been experimentally obtained, and they do not represent absolute values. Other values could be used with acceptable results and the present invention should not be regarded as limited to the specific values stated herein.

Figure 18:
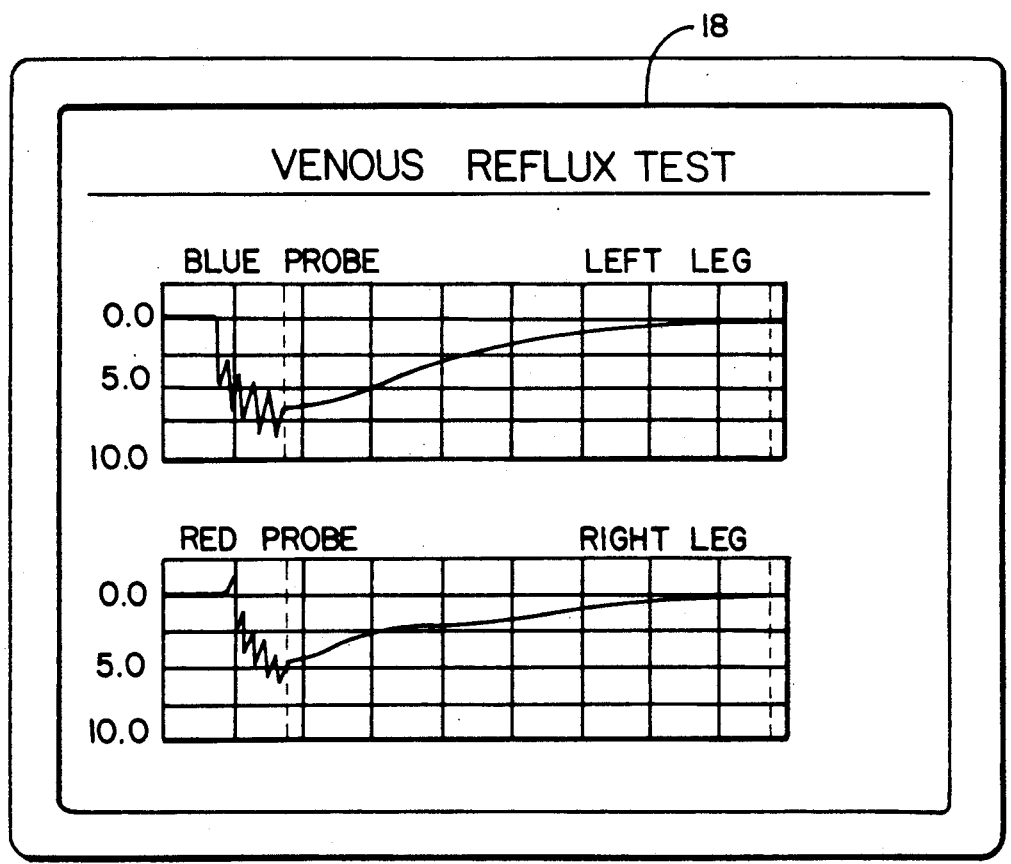
FIG. 18 is a representative display of the left and right PPG signals for the Venous Reflux test after automatic rescaling and after completion of the test.

Presuming the baseline value 480 is sufficiently stable, the method proceeds to step 408 which starts the real time data display as shown in FIG. 18. Step 410 is next initiated which visually and aurally cues the patient to flex on cue. These flexures are indicated by the region 484 of FIG. 17 which is really an indication of the blood being pumped out of the leg veins of the patient with each flexure. Immediately following the last flexure cue, a first caliper 486 is vertically placed on the real time display of FIG. 17 by step 412. Immediately thereafter, step 414 checks to see if the real time display needs to be re-scaled.

Figure 17A:
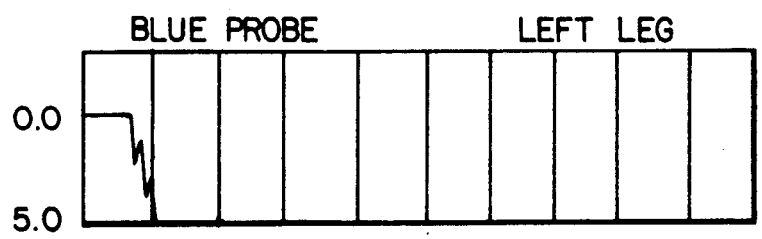
FIG. 17a is a representative display of the output signal from a PPG transducer for the Venous Reflux test before automatic rescaling of the display.

The rescaling process 414 is best understood by referring to FIG. 17a. Briefly, this process checks the signal amplitude of the PPG signal and re-scales the display if any of the datapoints fall outside the boundaries of the display as shown in FIG. 17a. In the preferred embodiment, five different scale sizes are available: size A, B, C, D, and E. Three of these scales B, C, and D are usually sufficient to display a full range of PPG signals. Since the PPG output signals are non-dimensional, any type of scale values can be used. In the preferred embodiment, if any of the PPG data points for both signals is greater than 5.0 (an arbitrary scale value), the display will be re-scaled to size "D". Likewise, if any of the data points for both signals are less than 2.0, the display will be re-scaled to size "B", otherwise, the display will be left in the default scale, size "C". Note that at all times during the test both the left and right displays will be set at the same size.

After the automatic rescaling process 414, the system continues to monitor the PPG output signals for both the left and right legs until a "plateau" is detected by decision process 416. When this "plateau" is detected, it is an indication that the leg veins have refilled. If a plateau is not detected after a certain maximum time period (78 seconds in the preferred embodiment), decision process 418 directs the system 10 to stop the scroll of the real time data display at 420 and place a 15 second caliper 488 (in FIG. 17) at this maximum time. A corresponding message 422 is displayed to inform the operator that the maximum time was reached and complete venous system refill (a plateau) was not detected.

In the preferred embodiment, the detection of the signal plateau is determined by looking at the data independently on each PPG output signal for 10 seconds. It has been found that a signal plateau can be identified by some empirically determined parameters. For example, if this data changes by less than:
19.5% of a division 482 for size "B"
7.8% of a division for size "C"
3.9% of a division for size "D"
and is within
1.25 divisions of the baseline 480 in size "C"
0.5 divisions of baseline in size "B"
2.5 divisions of baseline in size "D"
then a plateau exists, and the second caliper 488 is placed on the real time display at this point by process 424 and the test continues to step 426.

Step 426 automatically calculates the elapsed time between the first caliper 486 and the second caliper 488. This time is the venous refill time, or the time it took for the leg veins to refill with blood. The system 10 displays this number, along with an interpretation at step 428. If the refill time for both legs was greater than or equal to 20 seconds, it indicates normal venous valve operation. For normal and abnormal results, it gives the operator the option of changing the location of one or both of the calipers 486, 488. This option is allowed if the physician administering the test feels that the location at which the caliper was automatically placed was not ideal. If the second caliper 488 is moved, step 428 is re-executed and the refill time is re-calculated in accordance with the new caliper location. A new interpretation will also be displayed if necessary. In any event, if the refill time is still normal, the operator will be given the print option and a hard copy output of the test data and results will be printed by the printer 26. If the refill time was abnormal for one or both legs, the system will recommend at step 432 that the Venous Reflux tourniquet test be performed on one or both legs. The tourniquet test process is shown in detail in FIGS. 15b.

Generally, the Venous Reflux tourniquet test can take one of three paths, 434, 436, or 438 depending on whether the left, right or both legs require a tourniquet test. The steps for each process are essentially the same and will not be discussed in individual detail. A detailed discussion of the tourniquet test for the left leg provides a sufficient basis for understanding the operation of the other two.

The left leg tourniquet test begins by displaying a set of instructions for the operator at step 440. Essentially, these instructions direct the operator to place the appropriate pressure cuff (blue or red) around the patient's upper thigh. Process 442 starts the corresponding pressure cuff pump which inflates the cuff to approximately 60 mmHg of pressure. This pressure is sufficient to occlude the superficial veins in the legs, but not the arterial or deep venous system. As with the Quicklook ABI test 200, the system tests for the cuff not being connected and other pressure errors that might occur as previously discussed herein.

After the tourniquet cuff is inflated, the system proceeds to perform the standard Venous Reflux test as described above. As before, the operator is given the options to move the second, or plateau, caliper and the option for a hard copy output of the test data and results.

The tourniquet test for the right leg 436 is identical to the above described procedure, except that the test is performed on the patient's right leg. Similarly, the tourniquet test for both legs 438 is identical, except that the test is performed on both legs simultaneously.

Figure 19A:
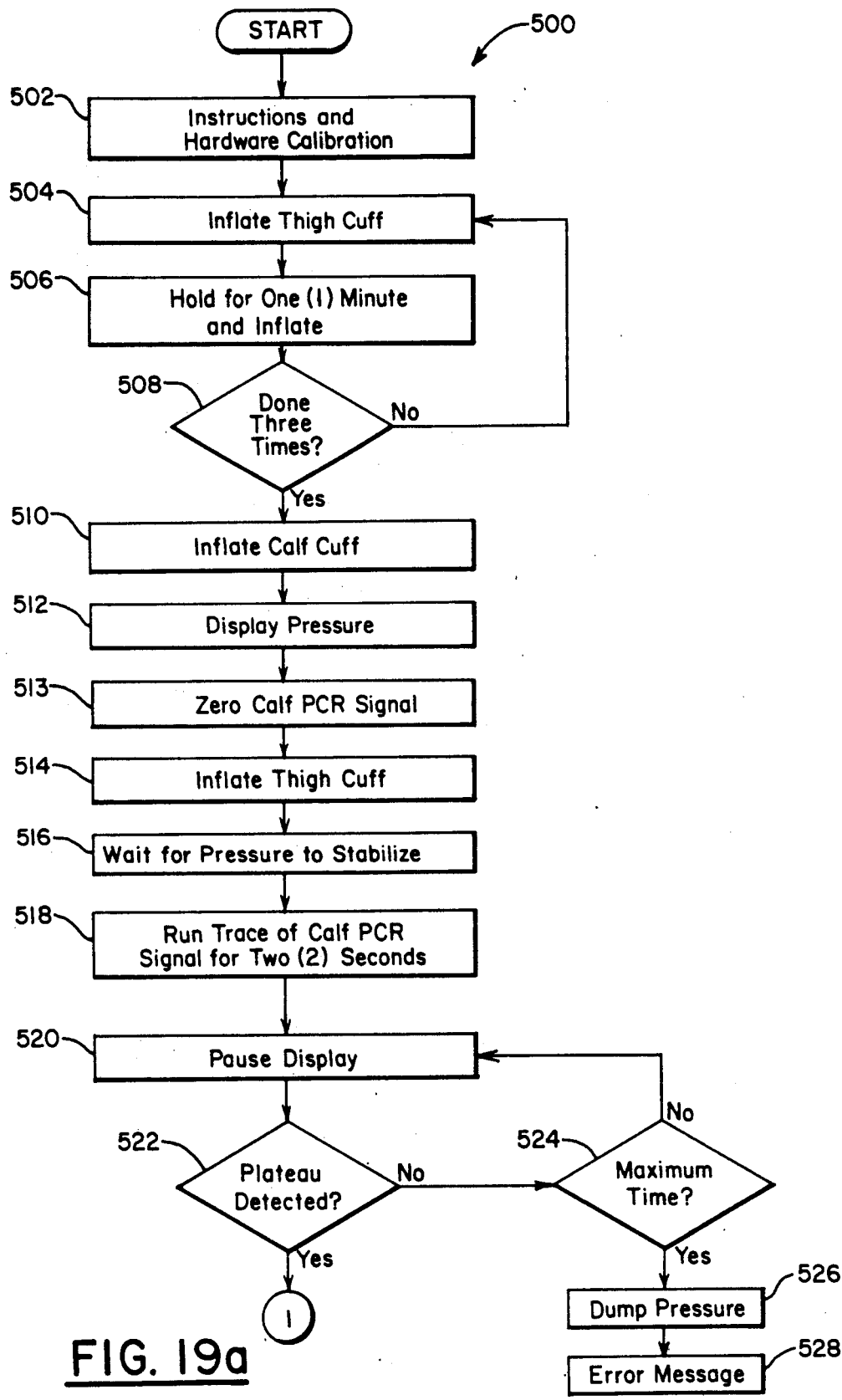
FIG. 19a is a detailed flow chart of the Maximum Venous Outflow test of the present invention.
Figure 19B:
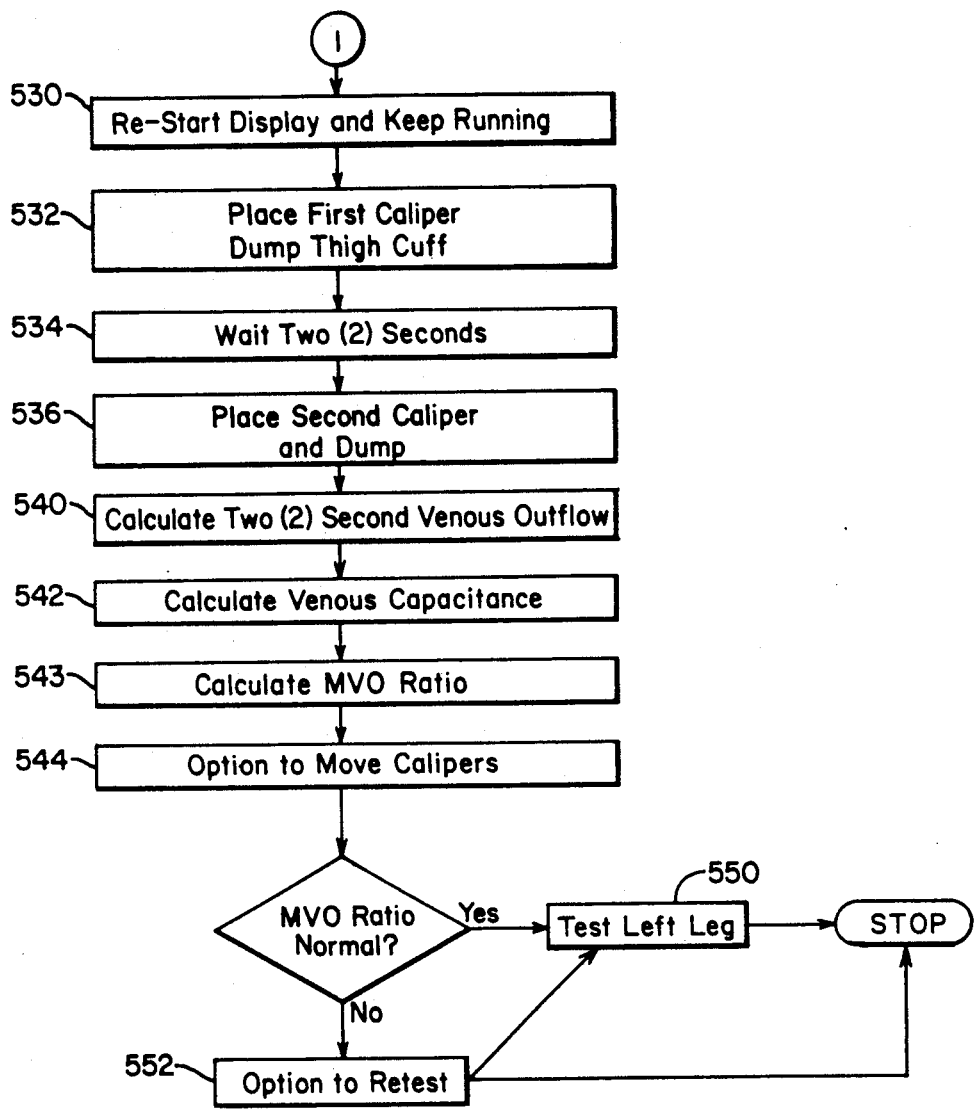
Figure 20:
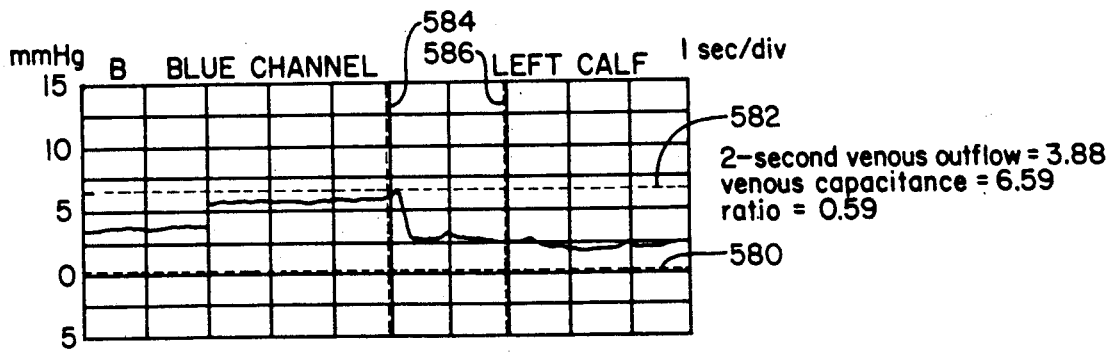
FIG. 20 is a representative display of the PCR output signal for the Maximum Venous Outflow test of the present invention.

Lastly, the maximum venous outflow test, or MVO test 500 is performed by the vascular testing system 10 as shown in FIGS. 19a, 19b and 20. Initially, the process begins at step 502 that displays the initial set-up instructions for the operator. These instructions basically instruct the operator to properly position the patient's leg and to wrap the MVO cuff around the patient's upper thigh and to wrap the calf or "blue" cuff 48 around the patient's calf. The process 502 also calibrates the pressure cuff transducers 41, 42.

Steps 504, 506, and 508 are executed to properly prepare the patient's venous system by stretching the leg veins as was earlier described. Specifically, process 504 actuates the thigh cuff pump 45 and solenoid valve 644, and inflates the MVO cuff to about 55 mmHg of pressure. This is enough pressure to occlude the leg veins, but not the arterial system. Thus, blood continues to flow into the leg, but cannot escape. This serves to stretch the leg veins which increases the accuracy of the test and the detectability of the plateau. As was described before, the system 10 also checks for proper cuff connection and other pressure errors. This pressure is held for one minute by step 506 and then released. This process of thigh cuff inflation and deflation is repeated twice more by process 508 in order to properly stretch the leg veins of the patient.

Step 510 is next executed which starts the actual test procedure by inflating the calf cuff 48 to about 15 mmHg. This step also checks for proper cuff connection and pressure errors as was earlier described. This cuff pressure is also displayed on the screen 18 during inflation and during the test as shown in FIG. 20.

Since the relevant data for this test comes from the calf cuff PCR waveform, this waveform is now zeroed by step 513. This zeroing point then serves as the baseline level about which all subsequent data will be measured. Step 514 next inflates the thigh cuff 47 by actuating its pump 45 to about 55 mmHg pressure. The pressure is allowed to stabilize by step 516. Step 518 starts the real time display of the calf cuff PCR waveform from the calf cuff transducer 42 for 2 seconds. This allows the operator to see that the testing process has begun and allows him or her to observe the current level of the signal. Step 520 pauses the screen display until a plateau is detected in the PCR waveform. If a plateau has not been detected after 2 minutes, process 524 immediately dumps the pressure in the thigh cuff at 526 and displays an error message 528.

The process 522 of determining a plateau is relatively simple. It has been empirically determined that a plateau exists if the PCR pressure data varies by less than 1 mmHg for a period of 15 seconds. If such a plateau is detected, the process proceeds to step 530.

Step 530 re-starts the real time display of the PCR waveform and keeps it running for the remainder of the test. After 4 seconds, the pressure in the thigh pressure cuff 47 is immediately dumped by process 532 which actuates the valve 43. This process 532 also places a first vertical caliper 584 on the real time display of the calf PCR waveform as shown in FIG. 20. Two seconds are allowed to pass at 534 before process 536 places a second vertical caliper 586 (FIG. 20) on the real time display and dumps the pressure in the calf cuff after the end of the real time display is reached.

Step 540 determines the "2 second venous outflow" by looking at the trace data and determining the difference in the amplitude of the trace at the time of the dump measured by the first caliper 584, and the amplitude of the trace 2 seconds after the dump. This number is then displayed on the screen 18.

Step 542 determines the venous capacitance by first placing an amplitude caliper 580 at the baseline level of the PCR trace. A second amplitude caliper 582 is then placed at the amplitude of the PCR waveform at the time of dump. The difference between these two amplitudes is calculated and displayed as the "venous capacitance." Finally, step 543 calculates the MVO ratio by dividing the 2-second or maximum venous outflow by the capacitance. This ratio is also displayed on the display screen 18.

Step 544 gives the operator the option to move the location of the amplitude caliper 582 if necessary. If it is re-located, the system will recalculate the venous capacitance, the 2 second venous outflow and the MVO ratio.

If the MVO ratio is abnormal, the operator is given the option to retest the patient at 552, or proceed to test the left leg 550. If the MVO ratio is normal, the operator is directed to repeat the above test on the patient's left leg at step 550. Finally, the operator is given the option to print out a hard copy of the test results.

This completes the description of the apparatus and method for vascular testing of the present invention. This foregoing description is considered as illustrative only of the principles of the invention. Further, since numerous modifications and changes will readily occur to those skilled in the art, it is not desired to limit the invention to the exact method as shown and described above. Accordingly, all suitable modifications and equivalents may be considered as falling within the scope of the invention as defined by the claims which follow.

The embodiments of the invention in which an exclusive property or privilege is claimed are defined as follows:

1. Vascular testing apparatus for determining the vascular condition of a patient, comprising:
   capillary blood flow detection means for detecting changes in the capillary blood flow of the patient and for generating capillary blood flow signals indicative of changes in the capillary blood flow of the patient;
   blood pressure detection means for detecting changes in the blood pressure of the patient and for generating blood pressure signals indicative of changes in the blood pressure of the patient;
   error detection means connected to said capillary blood flow detection means and to said blood pressure detection means for detecting whether said capillary blood flow detection means and said blood pressure detection means are functioning properly and that said capillary blood flow detection means and said blood pressure detection means are properly connected to the patient;
   display means having a scale for selectively displaying the capillary blood flow signals and the blood pressure signals;
   memory means for storing the capillary blood flow signals and the blood pressure signals;
   reproducing means for reproducing the capillary blood flow signals and the blood pressure signals in hard copy form; and,
   control means connected to said error detection means, said display means, said memory means, and said reproducing means for controlling and coordinating the operation thereof.

2. The vascular testing apparatus of claim 1 further comprising query means connected to said control means for querying an operator for a plurality of input data items.

3. The vascular testing apparatus of claim 2 further comprising instruction means connected to said control means and to said display means for displaying step-by-step instructions on the set-up and operation of said vascular testing apparatus.

4. The vascular testing apparatus of claim 3 further comprising hardware calibration means connected to said control means for automatically calibrating said blood flow detection means and said blood pressure detection means.

5. The vascular testing apparatus of claim 4 further comprising heart rate detection means connected to said control means for detecting the heart rate of the patient and for generating heart rate signals indicative of the heart rate of the patient.

6. The vascular testing apparatus of claim 5 wherein said capillary blood flow detection means further comprises photoplethysmography (PPG) transducer means for optically detecting changes in the capillary blood flow of the patient and for generating the capillary blood flow signals.

7. The vascular testing apparatus of claim 6 wherein said blood pressure detecting means further comprises pneumoplethysmography (PCR) transducer means for pneumatically detecting the blood pressure of the patient and for generating the blood pressure signals.

8. The vascular testing apparatus of claim 7 wherein said pneumoplethysmography (PCR) transducer means comprises:
a pressure cuff;
pump means pneumatically connected to said pressure cuff and connected to said control means for inflating said pressure cuff;
valve means pneumatically connected to said pressure cuff and connected to said control means for deflating said pressure cuff; and,
pressure transducer means pneumatically connected to said pressure cuff and to said control means for generating said blood pressure signals for said control means that are proportional to the pressure in said pressure cuff.

9. The vascular testing apparatus of claim 8, wherein said error detection means includes means to determine whether the patient is properly physically prepared for the testing procedure.

10. The vascular testing apparatus of claim 9, wherein said control means further comprises:
resizing means for automatically resizing the scale of said display means;
caliper placing means for automatically placing calipers at predetermined locations on said display means;
signal plateau detection means for detecting, according to a predetermined set of conditions, a plateau in the capillary blood flow signals and in the blood pressure signals.

11. The heart rate detection means of claim 5 further comprising:
slope detection means for determining the presence of signal peaks in the capillary blood flow signals; and
time calculation means for calculating an elapsed time between the signal peaks.

12. A method of determining the Ankle-Brachial Index Ratio (ABI ratio) of a patient with the aid of a computer including a brachial photoplethysmography (PPG) transducer for generating brachial blood flow signals having a plurality of signal peaks indicative of the brachial capillary blood flow and an ankle photoplethysmography (PPG) transducer for generating ankle blood flow signals having a plurality of signal peaks indicative of the changing ankle capillary blood flow of the patient, comprising the steps of:
determining the heart rate of the patient;
simultaneously inflating a brachial pressure cuff and an ankle pressure cuff, said brachial pressure cuff generating brachial blood pressure signals indicative of the brachial blood pressure of the patient and said ankle pressure cuff generating ankle blood pressure signals indicative of the ankle blood pressure of the patient;
continuously monitoring and displaying the brachial blood pressure signals and the ankle blood pressure signals;
determining when the brachial arteries and the ankle arteries of the patient have been occluded;
stopping the inflation of the brachial pressure cuff and the ankle pressure cuff when the respective brachial or ankle arteries have been occluded;
deflating the brachial pressure cuff and the ankle pressure cuff at a predetermined rate;
detecting when the brachial and the ankle arteries of the patient have re-opened;
storing and displaying the brachial blood pressure signals and the ankle blood pressure signals at the instant each respective brachial and ankle artery has re-opened;
deflating the brachial pressure cuff and the ankle pressure cuff;
calculating an ABI ratio; and,
displaying said ABI ratio.

13. The method of determining the Ankle-Brachial Index ratio of a patient of claim 12, wherein the step of displaying the brachial blood pressure signals and the ankle blood pressure signals further includes the step of continually updating the display of the brachial blood pressure signals and the ankle blood pressure signals.

14. The method of determining the Ankle-Brachial Index ratio of a patient of claim 13, wherein the step of determining when the brachial arteries and the ankle arteries are occluded is defined further to include the steps of:
determining a brachial maximum peak amplitude from the plurality of signal peaks, each of which has a brachial signal peak amplitude, from said brachial blood flow signals, and determining an ankle maximum peak amplitude from the plurality of signal peaks, each of which has an ankle signal peak amplitude, from said ankle blood flow signals;
calculating a brachial occlusion cut-off value and an ankle occlusion cut-off value based on the brachial maximum peak amplitude and on the ankle maximum peak amplitude, respectively;
comparing the brachial signal peak amplitude of the signal peaks from the brachial blood flow signals with the ankle signal peak amplitude of the signal peaks from the ankle blood flow signals as the brachial and ankle pressure cuffs are inflated and comparing the amplitude of each respective brachial and ankle signal peak to the previously determined corresponding brachial and ankle occlusion cut-off value; and
finding arterial occlusion when the amplitude of each respective brachial and ankle signal peak is less than or equal to the corresponding brachial and ankle occlusion cut-off value.

15. The method of claim 14, wherein the brachial occlusion cut-off value is about 75% of the brachial maximum peak amplitude and the ankle occlusion cut-off value is about 75% of the ankle maximum peak amplitude.

16. The method of determining the Ankle-Brachial Index ratio of a patient of claim 15 wherein the step of determining when the brachial arteries and the ankle arteries have re-opened is defined further to include the steps of:

continuously monitoring the brachial blood flow signals and the ankle blood flow signals after arterial occlusion has been found for both the brachial and ankle arteries for signal peaks that have a positive slope for a predetermined period of time; and determining whether a predetermined number of sequential signal peaks also have positive slopes for the predetermined period of time and also occur within a certain predetermined time frame of the previously calculated heart rate.

17. The method of claim 16, wherein the predetermined period of time is greater than or equal to about 48 milliseconds and less than about 180 milliseconds.

18. The method of claim 16, wherein the predetermined time frame of the previously calculated heart beat rate is defined to be about +/− 25% of the time around an expected time of an occurrence of a signal peak based on the previously calculated heart beat rate.

19. The method of determining the Ankle-Brachial Index ratio of claim 12, further comprising the step of continuously monitoring and storing the ankle blood pressure signals for a predetermined time before fully deflating the ankle pressure cuff.

20. The method of determining the Ankle-Brachial Index of a patient of claim 12 further comprising the step of: printing the test data and results in hard copy form.

21. A method of determining the competency of the valves in the leg veins in the leg of a patient, with the aid of a computer, comprising the steps of:

determining, in response to blood pressure signals from an occlusive cuff pressure value occurring when an occlusive cuff is inflated, that the leg veins in the leg of the patient are fully filled with blood;

continuously monitoring the blood pressure signals and displaying the blood pressure signals on a continuous scaled display;

curing the patient to flex his leg at predetermined flex intervals, including a first and last flex interval, and for a predetermined number of times;

rescaling the continuous scaled display of the blood pressure signals if necessary;

determining, in response to the blood pressure signals, when the veins in the leg of the patient have refilled with blood;

calculating an elapsed time between the last of said predetermined number of flex intervals and when the leg veins have refilled with blood; and, displaying the elapsed time.

22. The method of determining the competency of the leg veins of a patient of claim 21 wherein, both the right leg and the left leg of the patient are tested simultaneously.

23. The method of determining the competency of the leg veins of a patient of claim 21, further comprising the steps of:

comparing, in relation to established medical elapsed time ranges indicating a normal refill time, said elapsed time for the leg veins to refill and determining whether said elapsed time is normal; and, displaying a recommendation for further testing if said elapsed time is not normal.

24. The method of determining the competency of the valves in the leg veins of a patient of claim 21, wherein the step of determining, in response to the blood pressure signals, when the veins in the leg of the patient have refilled with blood is further defined to include the steps of:

determining, in response to the blood pressure signals from the occlusive cuff pressure value occurring when the occlusive cuff is inflated, a baseline level of the amount of blood in the leg veins of the patient before cuing the patient to flex his leg;

continuously monitoring the blood pressure signals after the last of said leg flex intervals and determining a rate of change with time in the amount of blood in the leg veins of the patient;

determining when the rate of change is below a predetermined amount; and, determining when the amount of blood in the leg veins of the patient has returned within a predetermined amount of the baseline level.

25. The method of determining the competency of the valves in the leg veins of a patient of claim 24, further comprising the step of placing first and second calipers on said continuous scaled display, said first caliper being placed on the continuous scaled display of the blood pressure signals to indicate the time of the last of said leg flex intervals, and said second caliper being placed on the continuous scaled display to indicate when the amount of blood in the leg veins of the patient has returned within the predetermined amount of the baseline level.

26. The method of determining the competency of the valves in the leg veins of a patient of claim 25, further comprising the step of printing out the continuous display of the amount of blood in the leg veins of the patient and printing out the refill time.

27. A method of determining the sufficiency of the venous outflow in the leg veins of a patient, the leg having a venous system and an arterial system, comprising the steps of:

determining, in response to calf blood pressure signals from an occlusive calf cuff pressure value occurring when an occlusive calf cuff is inflated, a baseline blood capacity level;

displaying said calf blood pressure signals on a display for a predetermined time, then pausing said display;

inflating a thigh pressure cuff to a pressure sufficient to occlude the venous system of the leg, but not the arterial system;

detecting, in response to said calf blood pressure signals, a venous capacitance level;

restarting said display indicating said calf blood pressure signals;

rapidly deflating said thigh pressure cuff;

continuously monitoring and displaying said calf blood pressure signals of the patient's leg;

determining, from said calf blood pressure signals, a final blood capacitance value indicating the amount of blood remaining in the leg venous system after a predetermined amount of time and subtracting the value indicating the amount of blood remaining in the leg venous system from the venous capacitance level to yield a maximum venous outflow value;

calculating a maximum venous outflow ratio by dividing the maximum venous outflow value by the venous capacitance level; and, displaying the maximum venous outflow ratio on said display.

28. The method of determining the sufficiency of the venous outflow in the leg veins of a patient of claim 27, further comprising the step of printing said display of the calf blood pressure signals and the maximum venous outflow ratio in hard copy form.

29. The method of determining the sufficiency of the venous outflow in the leg veins of a patient of claim 28, further comprising the step of preparing the leg veins of the patient for the test by pre-stretching the leg veins of the patient.

30. The method of determining the sufficiency of the venous outflow in the leg veins of a patient of claim 27, wherein the step of determining the venous capacitance further comprises the steps of:

monitoring the rate of change of the calf blood pressure signals; and, determining the venous capacitance level when said rate of change falls below a predetermined amount.

31. The method of determining the sufficiency of the venous outflow in the leg veins of a patient of claim 30, further comprising the step of placing calipers on the display of the calf blood pressure signals to indicate the baseline blood capacity level, the venous capacitance level, a time when the thigh pressure cuff was deflated, and the final blood capacitance level.

32. Vascular testing apparatus for determining the vascular condition of a patient, comprising:

photoplethysmography (PPG) transducer means for optically detecting changes in the capillary blood flow of the patient and for generating capillary blood flow signals indicative of the changes in the capillary blood flow of the patient;

blood pressure detection means for detecting changes in the blood pressure of the patient and for generating blood pressure signals indicative of the changes in the blood pressure of the patient;

error detection means connected to said photoplethysmography transducer means and to said blood pressure detection means for detecting whether said photoplethysmography transducer means and said blood pressure detection means are functioning properly and that said photoplethysmography transducer means and said blood pressure detection means are properly connected to the patient;

display means having a scale for selectively displaying the capillary blood flow signals and the blood pressure signals;

memory means for storing the capillary blood flow signals and the blood pressure signals;

reproducing means for reproducing the capillary blood flow signals and the blood pressure signals in hard copy form;

control means connected to said error detection means, said display means, said memory means, and said reproducing means for controlling and coordinating the operation thereof;

query means connected to said control means for querying an operator for a plurality of input data items;

instruction means connected to said control means and to said display means for displaying step-by-step instructions on the set-up and operation of said vascular testing apparatus;

hardware calibration means connected to said control means for automatically calibrating said blood flow detection means and said blood pressure detection means; and heart rate detection means connected to said control means for detecting the heart rate of the patient and for generating heart rate signals indicative of the heart rate of the patient.

33. The vascular testing apparatus of claim 32 wherein said blood pressure detecting means further comprises pneumoplethysmography (PCR) transducer means for pneumatically detecting the blood pressure of the patient and for generating the blood pressure signals.

34. The vascular testing apparatus of claim 33 wherein said pneumoplethysmography (PCR) transducer means comprises:

a pressure cuff;

pump means pneumatically connected to said pressure cuff and connected to said control means for inflating said pressure cuff;

valve means pneumatically connected to said pressure cuff and connected to said control means for deflating said pressure cuff; and pressure transducer means pneumatically connected to said pressure cuff and to said control means for generating said blood pressure signals for said control means that are proportional to the pressure in said pressure cuff.

35. The vascular testing apparatus of claim 34, wherein said control means further comprises:

resizing means for automatically resizing the scale of said display means;

caliper placing means for automatically placing calipers at predetermined locations on said display means;

signal plateau detection means for detecting, according to a predetermined set of conditions, a plateau in the capillary blood flow signals and in the blood pressure signals.

36. The heart rate detection means of claim 32 further comprising:

slope detection means for determining the presence of signal peaks in the capillary blood flow signals; and time calculation means for calculating an elapsed time between the signal peaks.

37. A method of determining the Ankle-Brachial Index Ratio (ABI ratio) of a patient with the aid of a computer including a brachial photoplethysmography (PPG) transducer for generating brachial blood flow signals having a plurality of signal peaks indicative of the brachial capillary blood flow and an ankle photoplethysmography (PPG) transducer for generating ankle blood flow signals having a plurality of signal peaks indicative of the changing ankle capillary blood flow of the patient, comprising the steps of:

determining the heart rate of the patient;

simultaneously inflating a brachial pressure cuff and an ankle pressure cuff, said brachial pressure cuff generating brachial blood pressure signals indicative of the brachial blood pressure of the patient and said ankle pressure cuff generating ankle blood pressure signals indicative of the ankle blood pressure of the patient;

continuously monitoring and displaying the brachial blood pressure signals and the ankle blood pressure signals and continually updating the display of the brachial blood pressure signals and the ankle blood pressure signals;

determining when the brachial arteries and the ankle arteries of the patient have been occluded by determining a brachial maximum peak amplitude from the plurality of signal peaks, each of which has a brachial signal peak amplitude, from said brachial blood flow signals, and determining an ankle maximum peak amplitude from the plurality of signal peaks, each of which has an ankle signal peak amplitude, from said ankle blood flow signals; calculating a brachial occlusion cut-off value and an ankle occlusion cut-off value based on the brachial maximum peak amplitude and on the ankle maximum peak amplitude, respectively, wherein the brachial occlusion cut-off value is about 75% of the brachial maximum peak amplitude and the ankle occlusion cut-off value is about 75% of the ankle maximum peak amplitude; comparing the brachial signal peak amplitude of the signal peaks from the brachial blood flow signals with the ankle signal peak amplitude of the signal peaks from the ankle blood flow signals as the brachial and ankle pressure cuffs are inflated and comparing the amplitude of each respective brachial and ankle signal peak to the previously determined corresponding brachial and ankle occlusion cut-off value; and finding arterial occlusion when the amplitude of each respective brachial and ankle signal peak is less than or equal to the corresponding brachial and ankle occlusion cut-off value;

stopping the inflation of the brachial pressure cuff and the ankle pressure cuff when the respective brachial or ankle arteries have been occluded;

deflating the brachial pressure cuff and the ankle pressure cuff at a predetermined rate;

detecting when the brachial and the ankle arteries of the patient have re-opened by continuously monitoring the brachial blood flow signals and the ankle blood flow signals after arterial occlusion has been found for both the brachial and ankle arteries for signal peaks that have a positive slope for a predetermined period of time that is greater than or equal to about 48 milliseconds and less than about 180 milliseconds;

determining whether a predetermined number of sequential signal peaks also have positive slopes for the predetermined period of time and also occur within a certain predetermined time frame of the previously calculated heart rate;

storing and displaying the brachial blood pressure signals and the ankle blood pressure signals at the instant each respective brachial and ankle artery has reopened;

deflating the brachial pressure cuff and the ankle pressure cuff;

calculating an ABI ratio; and displaying said ratio.

38. The method of claim 37 wherein the predetermined time frame of the previously calculated heart rate is defined to be about +/− 25% of the time around an expected time of an occurrence of a signal peak based on the previously calculated heart rate.

39. A method of determining the competency of the valves in leg veins in a leg of a patient with the aid of a computer, comprising the steps of:

determining, in response to blood pressure signals from an occlusive cuff pressure value occurring when an occlusive cuff is inflated, that the leg veins in the leg of the patient are fully filled with blood by determining, in response to the blood pressure signals from the occlusive cuff pressure value occurring when the occlusive cuff is inflated, a baseline level of the amount of blood in the leg veins of the patient before cuing the patient to flex his leg; continuously monitoring the blood pressure signals after the last of said leg flex intervals and determining a rate of change with time in the amount of blood in the leg veins of the patient; determining when the rate of change is below a predetermined amount; and determining when the amount of blood in the leg veins of the patient has returned within a predetermined amount of the baseline level;

continuously monitoring the blood pressure signals and displaying the blood pressure signals on a continuous scaled display;

cuing the patient to flex his leg at predetermined flex intervals, including a first and last flex interval, and for a predetermined number of times;

rescaling the continuous scaled display of the blood pressure signals, if necessary;

determining, in response to the blood pressure signals, when the veins in the leg of the patient have refilled with blood;

calculating an elapsed time between the last of said predetermined number of flex intervals and when the leg veins have refilled with blood;

displaying the elapsed time; and placing first and second calipers on said continuous scaled display, said first caliper being placed on the continuous scaled display of the blood pressure signals to indicate the time of the last of said leg flex intervals, and said second caliper being placed on the continuous scaled display to indicate when the amount of blood in the leg veins of the patient has returned within the predetermined amount of the baseline level.

40. The method of determining the competency of the valves in the leg veins of a patient of claim 39, further comprising the step of printing out the continuous display of the amount of blood in the leg veins of the patient and printing out the refill time.

41. A method of determining the sufficiency of the venous outflow in the leg veins of a patient, the leg having a venous system and an arterial system, with the aid of a computer, comprising the steps of:

preparing the leg veins of the patient for the test by pre-stretching the leg veins of the patient;

determining, in response to calf blood pressure signals from an occlusive calf cuff pressure value occurring when an occlusive calf cuff is inflated, a baseline blood capacity level;

displaying said calf blood pressure signals on a display for a predetermined time, then pausing said display;

inflating a thigh pressure cuff to a pressure sufficient to occlude the venous system of the leg, but not the arterial system;

detecting, in response to said calf blood pressure signals, a venous capacitance level;

restarting said display indicating said calf blood pressure signals;

rapidly deflating said thigh pressure cuff;

continuously monitoring and displaying said calf blood pressure signals of the patient's leg;

determining, from said calf blood pressure signals, a final blood capacitance value indicating the amount of blood remaining in the leg venous system after a predetermined amount of time and subtracting the value indicating the amount of blood remaining in the leg venous system from the venous capacitance level to yield a maximum venous outflow value;

calculating a maximum venous outflow ratio by dividing the maximum venous outflow value by the venous capacitance level;

displaying the maximum venous outflow ratio on said display; and printing said display of the calf blood pressure signals and the maximum venous outflow ratio in hard copy form.

42. The method of determining the sufficiency of the venous outflow in the leg veins of a patient of claim 41, wherein the step of determining the venous capacitance further comprises the steps of:

monitoring the rate of change of the calf blood pressure signals; and determining the venous capacitance level when said rate of change falls below a predetermined amount.

43. The method of determining the sufficiency of the venous outflow in the leg veins of a patient of claim 42, further comprising the step of placing calipers on the display of the calf blood pressure signals to indicate the baseline blood capacity level, the venous capacitance level, a time when the thigh pressure cuff was deflated, and the final blood capacitance level.

* * * * *